(12) United States Patent
Suzuki et al.

(10) Patent No.: US 6,416,503 B1
(45) Date of Patent: *Jul. 9, 2002

(54) MATRIX FOR IONTOPHORESES

(75) Inventors: Yasuyuki Suzuki; Katsumi Iga; Hiroaki Okada; Yukihiro Matsumoto, all of Suita (JP)

(73) Assignee: Hisamitsu Pharmaceutical Co., Inc., Saga (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/842,516

(22) Filed: Apr. 24, 1997

Related U.S. Application Data

(63) Continuation of application No. 08/307,451, filed on Sep. 21, 1994, now abandoned.

(30) Foreign Application Priority Data

| Sep. 22, 1993 | (JP) | 5-236454 |
| Dec. 1, 1993 | (JP) | 5-301860 |
| Dec. 9, 1993 | (JP) | 5-309511 |

(51) Int. Cl.[7] .................................. A61N 1/30
(52) U.S. Cl. .......................................... 604/501; 604/20
(58) Field of Search ............................ 604/20–21, 501; 607/115, 120, 149–153; 514/946

(56) References Cited

U.S. PATENT DOCUMENTS

| 4,474,570 A | * | 10/1984 | Ariura et al. | 604/20 |
| 5,006,108 A | * | 4/1991 | LaPrade | 604/20 |
| 5,042,975 A | * | 8/1991 | Chien et al. | 604/20 |
| 5,224,927 A | * | 7/1993 | Tapper et al. | 604/20 |
| 5,250,022 A | * | 10/1993 | Chien et al. | 604/20 |

* cited by examiner

Primary Examiner—Mark Bockelman
(74) Attorney, Agent, or Firm—Wenderoth, Lind & Ponack, L.L.P.

(57) ABSTRACT

To provide a practical matrix for iontophoresis with markedly improved drug availability. A system for iontophoreses, which comprises an anode side matrix and a cathode side matrix, wherein the anode side matrix contains a cationized drug and the cathode side matrix contains a water soluble acidic substance. A matrix for iontophoreses comprising a drug reservoir containing a drug, the drug reservoir having a thickness of less than 0.05 mm. Iontophoresis using the iontophoretic matrix of the present invention makes it possible to administer a drug to the body at high availability.

6 Claims, 11 Drawing Sheets

MATRIX FOR IONTOPHORESES

This application is a continuation of Ser. No. 08/307,451 filed Sep. 21, 1994 now abandoned.

FIELD OF INVENTION

The present invention relates to a new matrix for iontophoreses.

BACKGROUND OF THE INVENTION

Iontophoresis is a percutaneous absorption promoting system with electricity as an external stimulant. The principle behind it is that drug molecule penetration through the skin barrier is promoted as molecules charged positively in the electric field between the cathode and anode upon electric supply migrate from the anode to the cathode, while negatively charged molecules migrate from the cathode to the anode [see the Journal of Controlled Release, Vol. 18, pp. 213–220, 1992; Advanced Drug Delivery Review, Vol. 9, p. 119, 1992; Pharmaceutical Research, Vol. 3, pp. 318–326, 1986].

Recent advances in synthetic technology and gene engineering have made it possible to produce naturally-occurring peptides or proteins, or derivatives thereof obtained by altering the amino acid compositions thereof or chemically modifying them, in pure forms and in large amounts. Such substances are expected to be applied to pharmaceuticals. On the other hand, medication of these peptides or proteins, which exhibit various physiological activity in trace amounts, must be controlled rigorously to maximize their drug efficacy with minimum prevalence of side effects in particular diseases. For example, parathyroid hormone and active fragments thereof exhibit mutually opposite actions on bone, i.e., bone formation and bone destruction. These are used to treat osteoporosis by intermittent administration in which bone formation surpasses bone destruction.

However, such physiologically active peptides or proteins are generally known to be poorly absorbable because of decomposition by digestive juices in the gastrointestinal tract and hydrolysis by lytic enzymes secreted from the digestive wall. It is therefore common practice to administer these physiologically active peptides or proteins by injection, rather than oral administration, to obtain satisfactory efficacy. However, this practice poses significant pain on the patient, and a major burden associated with the impossibility of self-administration. This is especially true when intermittent multiple-dose administration is required as in the case of active fragments of parathyroid hormone.

In the field of pharmaceutical manufacture, iontophoresis, as a new drug delivery system potentially applicable to such physiologically active peptides and proteins, is now being extensively studied.

A device for iontophoresis equipped with a means of voltage control for switching the polarity of the voltage applied between a pair of electrodes each of which contains a drug is described in JP-A 224770/1992. A device for iontophoresis characterized by the containment of a drug in both cathode and anode, the cathode being kept at high pH and the anode at low pH is described in Canadian laid-open Patent Application No. 2042994. The effects of drug isoelectric point and electrode pH on drug absorbability in iontophoresis is described in U.S. Pat. No. 5,042,975. A plaster for iontophoresis wherein a water separation/supply layer is arranged between the electrode layer and the drug-containing layer with a tight-sealed inner cover outside the electrode layer is described in JP-A 102768/1988.

However, conventional methods of iontophoresis have a problem in practical use, because they possess drawbacks of unsatisfactory drug absorption and time-related reduction in absorbability. Against this background the present invention is aimed at providing a practical matrix for iontophoresis offering markedly improved drug availability.

SUMMARY OF THE INVENTION

While taking the present circumstances mentioned above into consideration, the present inventors pursued their studies on a matrix for iontophoresis offering markedly improved drug availability. As the result, the present inventors found that iontophoreisis with a matrix, which comprises a cationized drug on the anode side and a water-soluble acidic substance or a salt thereof on the cathode side, or which comprises a drug reservoir containing a drug or a salt thereof, the reservoir having a thickness of less than 0.05 mm, markedly improves the percutaneous absorbability of the drug or a salt thereof. Based on these findings, the present inventors made further studies to complete the present invention.

DETAILED DESCRIPTION OF THE INVENTION

By the following description, the detailed description of a system for iontophoreses, which comprises an anode side matrix and a cathode side matrix, wherein the anode side matrix contains a cationized drug and the cathode side matrix contains a water-soluble acidic substance, will be described.

This invention provides:

1) A system for iontophoreses, which comprises an anode side matrix and a cathode side matrix, wherein the anode side matrix contains a cationized drug and the cathode side matrix contains a water-soluble acidic substance;

2) A system according to 1), wherein the drug is cationized with a water-soluble carboxylic acid;

3) A system according to -2), wherein the carboxylic acid is an aliphatic carboxylic acid;

4) A system according to 1), wherein the acidic substance is a water-soluble organic acid;

5) A system according to 1), wherein the acidic substance is a water-soluble inorganic acid;

6) A system according to 1), wherein the acidic substance is an aliphatic carboxylic acid;

7) A system according to 3) or 6), wherein the aliphatic carboxylic acid is a $C_{2-6}$ aliphatic carboxylic acid;

8) A system according to 7), wherein the $C_{2-6}$ aliphatic carboxylic acid is citric acid;

9) A system according to 1), wherein the pH on the anode side is in the range of 1 to 5;

10) A system according to 1), wherein the drug is a physiologically active peptide having at least one basic functional group;

11) A system according to 10), wherein the molecular weight of the peptide is not more than 7,000;

12 A system according to 10), wherein the isoelectric point of the peptide is not less than 5.5;

13) A system according to 1), wherein the drug is a calcium regulatory hormone;

14) A system according to 13), wherein the calcium regulatory hormone is parathyroid hormone or its derivative, or salts thereof;

15) A system according to 13), wherein the calcium regulatory hormone is calcitonin or its derivative, or salts thereof;

16) A matrix for iontophoreses, which comprises a drug reservoir containing a drug, the reservoir having a thickness of less than 0.05 mm.

17) A matrix according to 16), wherein the drug reservoir is composed of a water-soluble polymer;

18) A matrix according to 17), wherein the polymer is a cellulose derivative;

19) A matrix according to 16), wherein the drug reservoir further comprises a water-soluble carboxylic acid;

20) A matrix according to 19), wherein the carboxylic acid is a $C_{2-6}$ aliphatic carboxylic acid;

21) A matrix according to 16), wherein the drug is a physiologically active peptide having at least one basic functional group;

22) A matrix according to 21), wherein the molecular weight of the peptide is not more than 7,000;

23) A matrix according to 21), wherein the isoelectric point of the peptide is not less than 5.5;

24) A matrix according to 16), wherein the drug is a calcium regulatory hormone;

25) A matrix according to 24), wherein the calcium regulatory hormone is parathyroid hormone or its derivative, or salts thereof;

26) A matrix according to 24), wherein the calcium regulatory hormone is calcitonin or its derivative, or salts thereof;

27) A method for iontophoreses, which comprises using the system as defined in 1) and supplying electric charge intermittently;

28) A method for iontophoreses, which comprises using the matrix as defined in 16) and supplying electric charge intermittently;

29) A method for iontophoreses according to 27) or 28), wherein the electric supply comprises a pulsating direct current;

30) A method for iontophoreses according to 27) or 28), wherein the electric supply comprises a continuous direct current; and 31) A method for iontophoreses according to 29) or 30), wherein the amperage of the direct current is in the range of about 0.01 to 4 $mA/cm^2$.

Any drug can be used for the present invention, as long as it is cationizable to a water-soluble form.

Preferable examples of such drugs include physiologically active peptides having at least one basic functional group. The molecular weight of the peptide is preferably not more than about 7,000, more preferably not more than about 6,000, and especially preferably not more than about 5,000. The isoelectric point of the water-soluble peptide is preferably not less than about 5.5, more preferably not less than about 6.

The water-solubility of a drug is defined as the oil-water partition coefficient (pc) between water and n-octanol. The oil-water pc of a drug is preferably not more than 1, more preferably not more than 0.1.

Oil-water pc can be determined by the method described in "Butsuri Kagaku Jikkenho" written by Jitsusaburo Samejima, Shokabo, 1961. More concretely, n-octanol and a buffer of pH 5.5 (1:1 by volume mixture) is placed in a test tube. The buffer is exemplified by Søerenzen buffer [Ergebnisse Der Physiology, 12, 393 (1912)], Clark-Lubs buffer [Journal of Bacteriology, 2(1), 109, 191 (1917)], MacIlvaine buffer [Journal of Biological Chemistry, 49, 183, (1921)], Michaelis buffer [Die Wasserstoffionenkonzentration, p.186 (1914)] and Kolthoff buffer [Biochemische Zeitschrift, 179,410 (1926)]. An appropriate amount of a drug is placed in the test tube, which is then stoppered and incubated at 25° C. with occasional vigorous shaking. When the drug appears to have dissolved in both liquid phases to reach an equilibrium, the liquid mixture is kept standing or centrifuged. A given amount is pipetted from each of the upper and lower layers and analyzed for drug concentration in each layer. The ratio of the drug concentration in the n-octanol layer to that in the water layer is an oil-water pc.

Examples of preferable physiologically active peptides as described above include oligo-peptides such as luteinizing hormone-releasing hormone (LH-RH), or its similarly active derivatives, or salts thereof [U.S. Pat. Nos. 3,853,837, 4,008,209 and 3,972,859, British Patent No. 1423083, Proceedings of the National Academy of Science, Vol. 78, pp. 6509–6512 (1981)], LH-RH antagonists, or salts thereof [U.S. Pat. Nos. 4,086,219, 4,124,577, 4,253,997 and 4,317, 815], insulin, somatostatin or its derivatives, or salts thereof [U.S. Pat. Nos. 4,087,390, 4,093,574, 4,100,117 and 4,253, 998], adrenocorticotropic hormone (ACTH), melanocyte-stimulating hormone (MSH), thyrotropin-releasing hormone (TRH) or its derivatives, or salts thereof (JP-A-121273/1975 and JP-A 116465/1977), parathyroid hormone (PTH) or its derivatives, or salts thereof [e.g., PTH(1→84), PTH(1→34); JP-A 32696/1993 and JP-A 247034/1992, and EP-A No. 510662, 477885 and 539491], vasopressin or its derivatives [e.g., desmopressin, Folia Endocrinologica Japonica, Vol. 54, No. 5, pp.676–691 (1978)], oxytocin, calcitonin or its derivatives, or salts thereof [Endocrinology, 1992, 131/6 (2882–2890], glucagon, gastrin, secretin, cholecystokinin, angiotensin, enkephalin or its derivatives, or salts thereof [U.S. Pat. No. 4277394 and EP-A No. 31567]; endorphin, kyotorphin, interleukins (I through XI), tuftsin, thymopoietin, thymic humoral factor (THF), blood thymic factor (FTS) or its derivatives, or salts thereof [U.S. Pat. No. 4,229,438], and other thymic factors [Igaku no Ayumi, Vol. 125, No. 10, pp. 835–843 (1983)], motilin, daynorphin, bombesin, neurotensin, cerulein, bradykinin, urokinase, substance P, polymyxin B, colistin, gramicidin, bacitracin, protein synthesis-stimulating peptide (British Patent No. 8232082), gastric inhibitory polypeptide (GIP), vasoactive intestinal polypeptide (VIP), platelet-derived growth factor (PDGF), and growth hormone-releasing factor (GRF, somatocrinin) and so on.

These physiologically active peptides may be of human origin, or from non-human animals, such as bovines, pigs, chickens, salmon and eels, from chimeras between humans and non-human animals. These physiologically active peptides may be active derivatives thereof with partially altered structure. Such physiologically active peptides include insulin of pig origin and calcitonin of pig, chicken, salmon or eel origin, or of human-salmon chimeric origin [Endocrinology, 1992, 131/6 (2885–2890)].

Preferable examples of the above-mentioned drugs include parathyroid hormone, its derivatives and salts thereof, calcitonin or its derivatives, or salts thereof, LH-RH, its similarly active derivatives or salts thereof, TRH, its derivatives or salts thereof, vasopressin, its derivatives and insulin. Among them parathyroid hormone, its derivatives or salts thereof and calcitonin or its derivatives, or salts thereof are especially preferable.

The amount of drug added to the anode may be any one, as long as it is sufficient to exhibit the desired drug effect, varying with kind of drug used, target mammals (e.g. mouse, rat, bovine, horse, monkey, man, etc.) and site of administration (e.g. arm, abdomen, back, etc.). For example, in the case of administering human parathyroid hormone, its derivative or salts thereof, to an adult (50 kg body weight), a matrix (1 g) contains the drug about 0.01–10% by weight, preferably about 0.03–8% by weight, and more preferably about 0.05–5% by weight.

The drug can be cationized by any method, as long as the drug is soluble in water while in a cationized state. Preferably, this cationization is carried out by bringing the drug into contact with a water-soluble carboxylic acid. Concretely, a water-soluble carboxylic acid is added to an aqueous solution or suspension of the drug to yield a uniform solution. In this case, the amount of water-soluble carboxylic acid added is preferably such that the anodic pH falls within the range from about 1 to 5, and more preferably about 3 to 4. More concretely, it is preferable that the ratio of the molar number of the drug to the molar equivalent number of the carboxylic acid (carboxylic acid molar number×carboxylic acid valency) be about 1:20 to 1:400, preferably about 1:40 to 1:400.

Preferable examples of water-soluble carboxylic acids as described above include water-soluble aliphatic carboxylic acids. More preferable examples of water-soluble aliphatic carboxylic acids include $C_{2-6}$ water-soluble aliphatic carboxylic acids. Especially preferable examples of water-soluble aliphatic carboxylic acids include $C_{2-6}$ water-soluble aliphatic mono-, di- and tri-carboxylic acids having 1 to 5 hydroxy groups. More concretely, examples of water-soluble mono-carboxylic acids as such include acetic acid, propionic acid, ascorbic acid, lactic acid, gluconic acid and glucuronic acid and so on. Examples of water-soluble di-carboxylic acids as such include oxalic acid, malonic acid, succinic acid, malic acid, tartaric acid, phthalic acid and maleic acid and so on. Examples of water-soluble tri-carboxylic acid as such include citric acid and so on. Especially examples of water-soluble carboxylic acids include acetic acid, propionic acid, ascorbic acid, lactic acid, gluconic acid, glucuronic acid, malonic acid, succinic acid, maleic acid, malic acid, tartaric acid and citric acid. Preferable examples of water-soluble caboxylic acids include acetic acid, propionic acid, ascorbic acid, lactic acid, gluconic acid, glucuronic acid, malonic acid, succinic acid, maleic acid, malic acid, tartaric acid and citric acid. More preferable examples of water-soluble caboxylic acids include citric acid, tartaric acid and succinic acid. Citric acid is especially preferable.

Water-soluble acidic substances on the cathode side include water-soluble organic acids and water-soluble inorganic acids. Physiologically non-active water-soluble acidic substances are preferable.

Preferable water-soluble organic acids as described above include water-soluble carboxylic acids. Preferable examples of water-soluble carboxylic acids include water-soluble aliphatic carboxylic acids. More preferable examples of water-soluble aliphatic carboxylic acids include $C_{2-6}$ water-solbule aliphatic carboxylic acids. Especially preferable examples of water-soluble aliphatic carboxylic acids include $C_{2-6}$ water-soluble aliphatic mono-, di- and tri-carboxylic acids having 1 to 5 hydroxy groups. More concretely, examples of water-soluble mono-carboxylic adds as such include acetic acid, propionic acid, ascorbic acid, lactic acid, gluconic acid and glucuronic acid and so on. Examples of water-soluble di-carboxylic acids as such include oxalic acid, malonic acid, succinic acid, malic acid, tartaric acid, phthalic acid and maleic acid and so on. Examples of water-soluble tri-carboxylic acids as such include citric acid and so on. Preferable examples of water-soluble carboxylic acids include acetic acid, propionic acid, ascorbic acid, lactic acid, gluconic acid, glucuronic acid, malonic acid, succinic acid, maleic acid, malic acid, tartaric acid and citric acid. More preferable examples of water-soluble carboxylic acids include succinic acid, tartaric acid and citric acid. Citric acid is especially preferable.

Preferable water-soluble inorganic acids include ortho-phosphoric acid, polyphosphoric acid, phosphorous acid and hydrochloric acid and so on.

Salts of such water-soluble acidic substances include salts of alkali metals (e.g. sodium, potassium and so on), ammonia, organic amines (e.g. alkylamines such as diethylamine and triethylamine and so on) and aromatic amines (e.g. pyridine, lutidine and so on) with the above-mentioned acid.

Furthermore orthophosphoric acid may be used as the ester with alcohol. The examples of the ester are methyl phosphate, ethyl phosphate and so on.

With respect to water-soluble carboxylic acids and water-soluble acidic substances, water solubility is expressed by the amount of water required to dissolve 1 g or 1 ml of the carboxylic acid or acidic substance at $20\pm5°$ C. In the present invention, it is preferable to use a carboxylic acid or acidic substance whose water solubility as determined as above is less than about 10 ml, more preferably less than 5 ml, and more preferably less than about 1 ml.

The amount of water-soluble acidic substance or salt thereof added to the cathode may be any one, as long as the skin is not adversely affected (irritation, corrosion etc.). Specifically, it is added at about 0.1–15% by weight, preferably about 0.1–12% by weight, more preferably about 0.3–10% by weight.

Any base can be used for the matrix to incorporate a drug, as long as it does not adversely affect the skin (irritation, corrosion etc.), is rich in skin contact property and is electroconductive. Preferable examples of bases include hydrophilic resins and polymers. Hydrophilic resins include acrylic resins (e.g. polyacrylamide, polyacrylic acid, alkali metal salts thereof and esters thereof and so on), vinyl resins (e.g. polyvinylpyrrolidone, polyvinyl alcohol, polyvinyl ethyl ether and copolymers thereof and so on), and natural polysaccharides (e.g. tragacanth gum and karaya gum and so on). Polymers include methyl cellulose, hydroxypropyl cellulose, hydroxypropylmethyl cellulose, hyaluronic acid and alkali metal salts thereof and so on.

A material such as cotton, filter paper or a membrane filter as impregnated with an electroconductivity-conferred drug-containing liquid, can also be used for the matrix.

The matrix is prepared to maintain its own shape, and extended into a film or sheet. Its thickness is preferably about 0.05 to 3.0 mm, especially preferably about 0.1 to 2.0 mm. Excess thickness may hinder percutaneous absorption of a drug.

The system for iontophoreses, which comprises an anode side matrix and a cathode side matrix, wherein the anode side matrix contains a cationized drug and the cathode side matrix contains a water-soluble acidic substance, is produced, for example, as follows:

A base for the above-described matrix to incorporate a drug is dissolved in water. To this solution, the drug and a compound for drug cationization are added, followed by kneading and shaping, to yield a matrix for anode. Separately, the base for the matrix is dissolved in water. To this solution, a water-soluble acidic substance or a salt thereof is added, followed by kneading and shaping, to yield a matrix for cathode. A system for iontophoreses is thus obtained.

In this practice, base (polyethylene glycol, propylene glycol, glycerol etc.) and dielectricity-conferring electrolytes (sodium chloride, sodium carbonate, phosphoric acid, sodium citrate etc.) are added to water as appropriate.

The amount of base used is such that the matrix retains its shape, varying depending on type of base, matrix shape (e.g. film, sheet and so on) and other factors. For example, the base is used in such amounts that the aqueous solution concentration is preferably about 0.1–30% by weight, more preferably about 0.5–20% by weight, and especially preferably about 1–15% by weight.

The contents of respective starting materials are chosen as appropriate to fall in the above mentioned ranges as in the finished product.

In the above-described production method, proteolytic enzyme inhibitors, isotonizing agents, preservatives, antioxidants, pH regulators, plasticizers, surfactants, osmolarity enhancers and other additives may be added as appropriate.

Proteolytic enzyme inhibitors include gabexate mesilate, α-1-antitrypsin, aprotinin and pepstatin, etc.

Isotonizing agents include mannitol and sorbitol, etc.

Preservatives include benzalkonium chloride, cetrimide (cetyltrimethylammonium bromide), benzoic acid, benzyl alcohol, Paraben (trade name for methyl-, ethyl-, propyl- and butyl-esters of p-hydroxybenzoic acid), chlorhexidine, chlorobutanol, phenylmercury acetate, phenylmercury borate, phenylmercury nitrate, potassium sorbate, sodium benzoate, sorbic acid and thiomersal (mercurithiosalicylate) and mixtures thereof, etc.

Antioxidants include sodium metabisulfite, butylated hydroxyanisole, butylated hydroxytoluene and mixtures thereof and so on.

pH regulators include citric acid and sodium citrate and so on.

Plasticizers include diethyl phthalate, dibutyl phthalate and tributyl citrate and so on.

Surfactants include sodium lauryl sulfate, diethylene glycol monostearate, propylene glycol monostearate, polyethylene glycol as commercially available under the trade name MACROGOL, polysorbate and polyvinyl alcohols and so on.

Osmolarity enhancers include dimethyl sulfoxide, N,N-dimethylacetamide, N,N-dimethylformamide, 2-pyrrolidone, N-methyl-2-pyrrolidone and 1-dodecylazacyclo-heptan-2-one and so on.

Iontophoresis using the system for iontophoreses of the present invention in combination with an appropriate power source by a per se known method makes possible safe percutaneous administration of a drug to mammals (e.g. mouse, rat, bovine, horse, monkey, man). Any power source can be used for this purpose, as long as it is capable of efficiently shifting thee drug into the body from the system for iontophoreses of the present invention Preferable power sources include power sources capable of applying continuous direct current or pulsating direct current to the matrix for iontophoreses of the present invention. More preferable power sources include power sources capable of applying pulsating direct current. Especially preferable power sources include power sources capable of applying rectangular pulsating direct current.

The amperage of the continuous direct current is preferably about 0.01 to 4 mA/cm$^2$, more preferably about 0.1 to 4 mA/cm$^2$.

The frequency of the pulsating direct current is preferably chosen over the range from about 0.1 to 200 kHz, more preferably about 1 to 100 kHz, and especially preferably about 5 to 80 kHz.

The on/off ratio of the pulsating direct current is preferably chosen over the range from about 1/100 to 20/1, more preferably about 1/50 to 15/1, and especially preferably about 1/30 to 10/1.

The amperage of the pulsating direct current is preferably chosen over the range from about 0.1 to 4 mA/cm$^2$, more preferably about 0.3 to 3.5 mA/cm$^2$, and especially preferably about 0.5 to 3 mA/cm$^2$.

Electric supply time is preferably shorter than 24 hours, more preferably shorter than 12 hours, and especially preferably shorter than 6 hours, for continuous supply.

As for electric supply method, it is preferable to repeat a continuous electric supply period of about 1 minute to 6 hours, more preferably about 1 minute to 2 hours, and especially preferably about 10 minutes to 1.5 hours, followed by a non-electric supply period of about 1 minute to 6 hours, more preferably about 10 minutes to 4 hours, and especially preferably about 30 minutes to 2 hours, at least two times. It is especially preferable to repeat the electric supply/non-supply cycle at least three times.

When the electric supply/non-supply cycle is repeated, it is preferable that the total electric supply period be about 10 minutes to 24 hours, more preferably about 30 minutes to 2 hours.

For iontophoresis in which the above-described electric supply/nonsupply cycle is repeated, pulsating direct current or continuous direct current, for instance, is used, with preference given to pulsating direct current. The frequency of this pulsating direct current is preferably about 1 to 100 kHz, more preferably about 20 to 60 kHz. The on/off ratio of the pulsating direct current is preferably about 10/1 to 1/10, more preferably about 3/1 to 1/3. The amperage of the pulsating direct current is preferably about 0.01 to 4.0 mA/cm$^2$, more preferably about 0.5 to 3.0 mA/cm$^2$, and especially preferably about 0.8 to 1.8 mA/cm$^2$.

The amperage of the continuous direct current is preferably about 0.01 to 4.0 mA/cm$^2$, more preferably about 0.01 to 1 mA/cm$^2$, and especially preferable about 0.05 to 0.3 mA/cm$^2$.

A system for iontophoreses, which comprises an anode side matrix and a cathode side matrix, wherein the anode side matrix contains a cationized drug and the cathode side matrix contains a water-soluble acidic substance, may be used as shown in FIG. 1 and 2.

By the following description, the detailed description of a matrix for iontophoreses, which comprises a drug reservoir containing a drug, the reservoir having a thickness of less than 0.05 mm, is will be described.

Any drug can be used for the present invention, as long as it is percutaneously absorbable. Preferably, a percutaneously absorbable, cationizable drug that is water-soluble while in a cationized state, is used.

Preferable examples of such drugs include physiologically active peptides having at least one basic functional group (e.g., amino group), or non-peptide drugs having at least one basic functional group. More preferable examples of such drugs include physiologically active peptides having at least one basic functional group. The molecular weight of the peptide is preferably not more than about 7,000, more preferably not more than about 6,000, and especially preferably not more than about 5,000. The isoelectric point of the water-soluble peptide is preferably not less than about 5.5, more preferably about 5.5 to 13, and especially preferably about 6 to 12.

The water-solubility of a drug is defined as the oil-water partition coefficient (pc) between water and n-octanol. The oil-water pc of a drug is preferably not more than 1, more preferably not more than 0.1.

Oil-water pc can be determined by the method described in "Butsuri Kagaku Jikkenho" written by Jitsusaburo Samejima, Shokabo, 1961. More concretely, n-octanol and a buffer of pH 5.5 (1:1 by volume mixture) is placed in a test tube. The buffer is exemplified by Søerenzen buffer [Ergebnisse Der Physiology, 12, 393 (1912)], Clark-Lubs buffer [Journal of Bacteriology, 2(1), 109, 191 (1917)], MacIlvaine buffer [Journal of Biological Chemistry, 49, 183, (1921)], Michaelis buffer [Die Wasserstoffionenkonzentration, p. 186 (1914)] and Kolthoff buffer [Biochemische Zeitschrift, 179, 410 (1926)]. An appropriate amount of a drug is placed in the test tube, which is then stoppered and incubated at 25° C. with occasional vigorous shaking. When the drug appears to have dissolved in both liquid phases to reach an equilibrium, the liquid mixture is kept standing or centrifuged. A given amount is pipetted from each of the upper and lower layers and analyzed for drug concentration in each layer. The ratio of the drug concentration in the n-octanol layer to that in the water layer is an oil-water pc.

Examples of preferable physiologically active peptides as described above include oligo-peptides such as luteinizing hormone-releasing hormone (LH-RH) or its similarly active derivatives, or salts thereof [U.S. Pat. Nos. 3,853,837, 4,008,209 and 3,972,859, British Patent No. 1423083, Proceedings of the National Academy of Science, Vol. 78, pp. 6509–6512 (1981)], LH-RH antagonists or salts thereof [U.S. Pat. Nos. 4,086,219, 4,124,577, 4,253,997 and 4,317,815], insulin, somatostatin or its derivatives, or salts thereof [U.S. Pat. Nos. 4,087,390, 4,093,574, 4,100,117 and 4,253,998], adrenocorticotropic hormone (ACTH), melanocyte-stimulating hormone (MSH), thyrotropin-releasing hormone (TRH) or its derivatives, or salts thereof (JP-A 121273/1975 and JP-A 116465/1977, parathyroid hormone (PTH) or its derivatives, or salts thereof [e.g., PTH(1→84), PTH(1→34); JP-A 32696/1993 and JP-A 247034/1992, and EP-A No. 510662, 477885 and 539491], vasopressin or its derivatives [e.g., desmopressin, Folia Endocrinologica Japonica, Vol. 54, No. 5, pp. 676–691 (1978)], oxytocin, calcitonin or its derivatives, or salts thereof [Endocrinology, 1992, 13116 (2882–2890)], glucagon, gastrin, secretin, cholecystokinin, angiotensin, enkephalin, or its derivatives, or salts thereof [U.S. Pat. No. 4,277,394 and EP-A No. 31567]; endorphin, kyotorphin, interleukins (I through XI), interferon ($\alpha$, $\beta$ and $\gamma$), superoxidedismutase, tuftsin, thymopoietin, thymic humoral factor (THF), blood thymic factor (FTS) or its derivatives, or salts thereof [U.S. Pat. No. 4,229,438], and other thymic factors [Igaku no Ayumi, Vol.125, No. 10, pp. 835–843 (1983)], motilin, dinorphin, bombesin, neurotensin, cerulein, bradykinin, urokinase, substance P, polymyxin B, colistin, gramicidin, bacitracin, protein synthesis-stimulating peptide (British Patent No. 8232082), gastric inhibitory polypeptide (GIP), vasoactive intestinal polypeptide (VIP), platelet-derived growth factor (PDGF), and growth hormone-releasing factor (GRF, somatocrinin) and so on.

These physiologically active peptides may be of human origin, or from non-human animals, such as bovines, pigs, chickens, salmon and eels, from chimeras between humans and non-human animals. These physiologically active peptides may be active derivatives thereof with partially altered structure. Such physiologically active peptides include insulin of pig origin and calcitonin of pig, chicken, salmon or eel origin, or of human-salmon chimeric origin [Endocrinology, 1992, 131/6 (2885–2890)].

Preferable examples of the above-mentioned drugs include parathyroid hormone, its derivatives and salts thereof, calcitonin or its derivatives, or salts thereof, LH-RH, its similarly active derivatives or salts thereof, TRH, its derivatives or salts thereof, vasopressin, its derivatives and insulin. Among them parathyroid hormone, its derivatives or salts thereof and calcitonin or its derivatives, or salts thereof are especially preferable.

Preferable non-peptide drugs include narcotic sedatives (e.g. morphine and buprenorphine and so on), angina pectoris remedies (e.g. isosorbide dinitrate and propranolol and so on), fentanyl, scopolamine, lidocaine and pilocarpine, etc.

The drug contained in the drug reservoir of the present invention may be partially or completely dissolved, or dispersed therein.

The amount of drug added to the drug reservoir may be any one, as long as it is sufficient to exhibit the desired drug effect, varying with kind of drug used, target mammals (e.g. mouse, rat, bovine, horse, monkey, man, etc.) and site of administration (e.g. arm, abdomen, back, etc.). For example, in the case of administering of human parathyroid hormone, its derivative or salts thereof, an adult (50 kg body weight), a matrix (1 g) contain the drug preferably about 0.01 to 20% by weight, more preferably about 0.03–16% by weight, and especially preferably about 0.05 to 14% by weight. Preferably, the matrix as such is used in an amount of about 0.02 to 1 g, more preferably about 0.05 to 0.5 g in each use.

The drug reservoir of the present invention is preferably thin, as long as it retains its original form. Concretely, the thickness is preferably less than 0.05 mm, more preferably about 0.005 to 0.05 mm, and especially preferably about 0.01 to 0.03 mm.

The weight of the matrix is preferably about 0.02 to 2 g, especially preferably about 0.05 to 0.5 g.

The drug reservoir of the present invention may have any shape, as long as it is compatible with the skin to ensure desired absorption. Examples of such shapes include circular, oblong, square or rectangular films and sheets and so on. The cross-sectional area is preferably about 0.5 to 150 $cm^2$, more preferably about 1 to 50 $cm^2$.

A preferable base used to produce the drug reservoir of the present invention is a water-soluble polymer having a water solubility of not less than 10% (w/v) at 20±5° C. and capable of film formation. Such water-soluble polymers include the polymeric water-soluble film bases in common use for film coating of tablets etc., described in Pharm Tech Japan, Vol. 7, pp. 51–79 (1991). More concretely, water-soluble cellulose derivatives (e.g. hydroxypropyl cellulose, hydroxypropylmethyl cellulose), water-soluble polysaccharides (e.g. dextrin, pullulan, sodium alginate) and water-soluble proteins (e.g., gelatin) may be mentioned. Water-soluble cellulose derivatives are especially preferable. These film bases may be used singly or in combination.

In addition to the above-described base for the drug reservoir, there may be incorporated substances that do not form a drug reservoir by themselves but improve drug reservoir properties or are capable of controlling drug release by altering the rate of reaction with water or the viscosity after reaction when used as additives. Such substances include polyethylene glycols of various molecular weights (e.g., PEG-6000 and so on), polyvinyl alcohol, polyvinylpyrrolidone, carboxyvinyl polymer, albumin, collagen, agar, glycerol, various amino acids, sugars (e.g. sucrose, glucose and mannitol and so on), and surfactants (e.g. Tween 80 and HCO 60 and so on), etc.

There may also be incorporated dissolution aids (e.g., cyclodextrins such as $\alpha$-CD, $\beta$-CD, $\gamma$-CD and so on) for facilitating percutaneous absorption of each drug, antioxidants (e.g., vitamins C and E, etc.) and drug absorption promoters (e.g., azon, fatty acids, etc.). When the drug is a physiologically active peptide, there may be incorporated enzyme inhibitors (e.g. aprotinin, camostat mesilate, chymostatin and so on) to prevent drug decomposition in the drug reservoir.

Also, to provide high absorbability by conferring a water retention property on the skin, liposomes etc. as prepared from urea, hyaluronic acid, lecithin, ceramide, synthetic lipid or the like may be added.

In addition to the above additives, film bases that are not necessarily soluble in water or film bases that dissolve within a particular pH range (Pharm Tech Japan, Vol. 7, pp. 51–79, 1991) may be added in appropriate amounts, to control drug release. Such film bases include methyl cellulose, ethyl cellulose, hydroxypropylmethyl cellulose, hydroxypropylmethyl cellulose phthalate, hydroxypropylmethyl cellulose acetate succinate, carboxymethyl cellulose sodium, carboxymethylethyl cellulose, cellulose acetate phthalate, hydroxyethyl cellulose, alpha-starch, aminoacrylmethacrylate copolymers (Eudragit E, Eudragit RS), methacrylic acid copolymers (Eudragit L, Eudragit S), alginic acid propylene glycol ester (Kimiloid), purified shellac and white shellac, or the like.

The content ratios of additives other than the above film bases are not subject to limitation, as long as the desired film properties are retained.

The drug reservoir of the present invention may further contain a water-soluble carboxylic acid. In this case, the amount of water-soluble carboxylic acid added is preferably such that the ratio of the molar number of the drug to the molar equivalent number of the carboxylic acid (carboxylic acid molar number×carboxylic acid valency) be about 1:20 to 1:400, preferably about 1:40 to 1:400.

Preferable examples of water-soluble carboxylic acids as described above include water-soluble aliphatic carboxylic acids. More preferable examples of water-soluble aliphatic carboxylic acids include $C_{2-6}$ water-soluble aliphatic carboxylic acids. Especially preferable examples of water-soluble aliphatic carboxylic acids include $C_{2-6}$ water-soluble aliphatic mono-, di- and tri-carboxylic acids having 1 to 5 hydroxy groups. More concretely, examples of water-soluble mono-carboxylic acids as such include acetic acid, propionic acid, ascorbic acid, lactic acid, gluconic acid and glucuronic acid and so on. Examples of water-soluble di-carboxylic acids as such include oxalic acid, malonic acid, succinic acid, malic acid, tartaric acid, phthalic acid and maleic acid and so on. Examples of water-soluble tri-carboxylic acids as such include citric acid and so on. Preferable examples of water-soluble carboxylic acids include acetic acid, propionic acid, ascorbic acid, lactic acid, gluconic acid, glucuronic acid, malonic acid, succinic acid, maleic acid, malic acid, tartaric acid and citric acid or the like. More preferable examples of water-soluble carboxylic acids include succinic acid, tartaric acid and citric acid. Citric acid is especially preferable.

With respect to water-soluble carboxylic acids, water solubility is expressed by the amount of water required to dissolve 1 g or 1 ml of the carboxylic acid at 20±5° C. In the present invention, it is preferable to use a carboxylic acid whose water solubility as determined as above is less than about 10 ml, more preferably less than 5 ml, and more preferably less than about 1 ml.

The drug reservoir of the present invention is produced, for example, as follows: A base for the above-described drug reservoir to incorporate a drug is dissolved in solvent. In this solution, the drug is dissolved or dispersed, and if necessary, various additives as described above are added, followed by kneading to a uniform mixture, after which the mixture is poured in a mold and dried in a refrigerator or a desiccant-containing desiccator or allowed to dry at 20±5° C., or dried under reduced pressure (e.g., about 0.01 to 0.1 atm) with heating (e.g., about 30–60° C.) or lyophilized, to yield the desired drug reservoir.

The examples of above-described solvent include water, ketone (e.g. acetone, ethyl methyl ketone and so on), alcohol (e.g. ethanol, methanol and so on) or the like.

In this practice, base (polyethylene glycol, propylene glycol, glycerol etc.) and dielectricity-conferring electrolytes (e.g. sodium chloride, sodium carbonate, phosphoric acid, sodium citrate etc.) are added to water as appropriate.

The amount of base used is such that the matrix retains its self-shaping property, varying depending on kind of base, matrix shape (e.g. film, sheet and so on) and other factors. For example, the base is used in such amounts that the aqueous solution concentration is preferably about 0.1–30% by weight, more preferably about 0.5–20% by weight, and especially preferably about 1–15% by weight.

The contents of respective starting materials are chosen as appropriate to fall in the above mentioned ranges in the finished product.

To ensure accurate administration of the present plaster to a site of administration, it is preferable that one face of the drug reservoir is in gentle adhesion to another supporting film, and it easily peels off from the supporting film upon contact with an electrode matrix for iontophoreses and accurately adheres to the face of administration. Such supporting film materials include paper and plastic materials coated with wax, silicon, latex or fluorine resin.

Iontophoresis using the iontophoretic matrix of the present invention in combination with an appropriate power source by a per se known method makes possible safe percutaneous administration of a drug to mammals (e.g. mouse, rat, bovine, horse, monkey, man). Any power source can be used for this purpose, as long as it is capable of efficiently shifting the drug into the body from the matrix for iontophoreses of the present invention.

Preferable power sources include power sources capable of applying continuous direct current or pulsating direct current to the matrix for iontophoreses of the present invention. More preferable power sources include power sources capable of applying pulsating direct current. Especially preferable power sources include power sources capable of applying rectangular pulsating direct current.

The amperage of the continuous direct current is preferably about 0.01 to 4 mA/cm$^2$, more preferably about 0.1 to 4 mA/cm$^2$.

The frequency of the pulsating direct current is preferably chosen over the range from about 0.1 to 200 kHz, more preferably about 1 to 100 kHz, and especially preferably about 5 to 80 kHz.

The on/off ratio of the pulsating direct current is preferably chosen over the range from about 1/100 to 20/1, more preferably about 1/50 to 15/1, and especially preferably about 1/30 to 10/1.

The amperage of the pulsating direct current is preferably chosen over the range from about 0.1 to 4 mA/cm$^2$, more preferably about 0.3 to 3.5 mA/cm$^2$, and especially preferably about 0.5 to 3 mA/cm$^2$.

Electric supply time is preferably shorter than about 24 hours, more preferably shorter than about 12 hours, and especially preferably shorter than about 6 hours, for continuous supply.

As for electric supply method, it is preferable to repeat a continuous electric supply period of about 1 minute to 6 hours, more preferably about 1 minute to 2 hours, and especially preferably about 10 minutes to 1.5 hours, followed by a non-electric supply period of about 1 minute to 6 hours, more preferably about 10 minutes to 4 hours, and especially preferably about 30 minutes to 2 hours, at least two times. It is especially preferable to repeat the electric supply/non-supply cycle at least three times.

When the electric supply/non-supply cycle is repeated, it is preferable that the total electric supply period be about 10 minutes to 24 hours, more preferably about 30 minutes to 2 hours.

For iontophoresis in which the above-described electric supply/nonsupply cycle is repeated, pulsating direct current or continuous direct current, for instance, is used, with preference given to pulsating direct current. The frequency of this pulsating direct current is preferably about 1 to 100 kHz, more preferably about 20 to 60 kHz. The on/off ratio of the pulsating direct current is preferably about 10/1 to 1/10, more preferably about 3/1 to 1/3. The amperage of the pulsating direct current is preferably about 0.01 to 4.0 mA/cm$^2$, more preferably about 0.5 to 3.0 mA/cm$^2$, and especially preferably about 0.8 to 1.8 mA/cm$^2$.

The amperage of the continuous direct current is preferably about 0.01 to 4.0 mA/cm$^2$, more preferably about 0.01 to 1 mA/cm$^2$, and especially preferable about 0.05 to 0.3 mA/cm$^2$.

The matrix for iontophoreses of the present invention, which comprises a drug reservoir containing a drug, the reservoir having a thickness of less than 0.05 mm, and a electrode matrix, can be used in anode or cathode, it is especially preferable to use it in the anode.

EXAMPLES

By the following Reference Example, Examples and Experimental Examples, the present invention,which is concerned with a system for iontophoreses, which comprises an anode side matrix and a cathode side matrix, wherein the anode side matrix contains a cationized drug and the cathode side matrix contains a water-soluble acidic substance, will be described in further detail, but they do not intend to limit the invention in any manner.

Percent figures in Reference Example are % by volume and those in Examples and Experimental Examples are % by weight/volume, unless otherwise stated.

Reference Example 1

Synthesis and purification of acetate salt of active fragment comprising amino acids from the amino terminus to No. 34 position of human parathyroid hormone (hereinafter referred to as hPTH) [hereinafter referred to as hPTH (1→34)].

The title peptide hPTH (1→34) was synthesized in accordance with a modification of the solid phase peptide synthesis method developed by Merrifield et al. [R. B. Merrifield, Advances in Enzymology, Vol. 32, pp. 221–296 (1969)], using an automatic peptide synthesizer 430A (Applied Biosystems, USA). Protected peptide-resin was synthesized per the protocol specified by Applied Biosystems. To protect the α-amino group of each amino acid at condensation, a tertiary butyloxycarbonyl (BOC) group was used. Side functional groups were protected as follows: The hydroxyl groups of serine and threonine were protected as o-benzyl ether; the carboxyl groups of glutamic acid and aspartic acid were protected as benzyl ester; the imidazole nitrogen of histidine was protected with benzyloxymethyl; the side chain amino group of lysine was protected with 2-chlorobenzyloxycarboxyl; the guanidine functional group of arginine was protected with a p-toluenesulfonyl group; the indolimine of tryptophan was protected with a formyl group. All amino acids were purchased from Applied Biosystems Japan or Bachem Chemicals.

To the starting material Boc-L-phenylalanine-p-oxymethylphenylacetamidomethyl resin (polystyrene-1% divinylbenzene), protected amino acids were condensed one by one. After all amino acids were condensed onto the resin, the protected peptide resin was taken out from the synthesizer and dried. The peptide resin (1 g) was reacted with anhydrous hydrogen fluoride (8 ml) containing p-cresol (1 ml), 1,2-ethanedithiol (1 ml) and 2-mercaptopyridine (100 mg) at 0° C. for 2 hours. After completion of the reaction, the hydrogen fluoride was distilled off, then the residue was washed with diethyl ether to remove almost all the reagent mixture. The resulting peptide was extracted with 3% acetic acid (10 ml) and filtered to remove the resin. The filtrate was purified by gel filtration using Sephadex G-25 (Pharmacia, Sweden). The gel filtration conditions were: column size 2.8×60 cm, detection wavelength 230 or 280 nm, solvent 3% acetic acid, flow rate 40 ml/hr. The peptide-containing fraction was collected and lyophilized, then the resulting standard powder preparation was further purified by reversed-phase high performance liquid chromatography using a column of YMC-Pack A-324 ODS (10×250 mm), eluent A=0.1% trifluoroacetic acid—99.9% water, eluent B=0.1% trifluoroacetic acid—99.9% acetonitrile, eluent density gradient program=0 minute (90% A+10% B) and 30 minutes (60% A+40% B), elution rate 1.6 ml/min, detection wavelength 230 or 280 nm. The peak fraction containing the desired product in pure form was collected and passed through a column of Bio-Rad AGI×8 (acetic acid type, 1.8×5 cm). The effluent was combined with column washings, and the acetonitrile was distilled off, followed by lyophilization, to yield 105 mg of hPTH (1→34). After hydrolysis with 6 N hydrochloric acid in a reduced-pressure tight tube at 110° C. for 24 hours in the presence of 4% thioglycollic acid, the following amino acid analytical values were obtained. Figures in parentheses are theoretical values.

Asp 4.00 (4); Ser 2.54 (3); Glu 4.92 (5); Gly 0.91 (1); Val 2.61 (3); Met 1.97 (2); Ile 0.83 (1); Len 4.90 (5); Phe 0.91 (1); Lys 2.82 (3); His 2.48 (3); Trp 0.76 (1); Arg 1.74 (2).

Example 1 hPTH (1→34) (10 mg) as produced in Reference Example 1 and citric acid monohydrate (7 mg) were dissolved in an 8% aqueous solution of polyvinyl alcohol (1 g) (pH 3.8), followed by gelatinization and shaping into a cylinder of 8 cm$^2$ in cross-sectional area and 1 mm in thickness for an iontophoretic matrix for anode. Citric acid monohydrate (7 mg) was dissolved in 1 g of an 8% aqueous solution of polyvinyl alcohol, followed by gelatinization and shaping into a cylinder of 8 cm$^2$ in cross-sectional area and 1 mm in thickness for an iontophoretic matrix for cathode.

Example 2 hPTH (1→34) (10 mg) and citric acid monohydrate (70 mg) were dissolved in an 8% aqueous solution of polyvinyl alcohol (1 g) (pH 2.8), followed by gelatinization and shaping into a cylinder of 8 cm$^2$ in cross-sectional area and 1 mm in thickness for an iontophoretic matrix for anode. Citric acid monohydrate (70 mg) was dissolved in an 8% aqueous solution of polyvinyl alcohol (1 g), followed by gelatinization and shaping into a cylinder of 8 cm$^2$ in cross-sectional area and 1 mm in thickness for an iontophoretic matrix for cathode.

Example 3

HPTH (1→34) (10 mg) and citric acid monohydrate (7 mg) were dissolved in an 8% aqueous solution of polyvinyl alcohol (0.4 g) (pH 3.8), followed by gelatinization and shaping into a cylinder of 3.2 cm$^2$ in cross-sectional area and 1 mm in thickness for an iontophoretic matrix for anode. Citric acid monohydrate (7 mg) was dissolved in an 8% aqueous solution of polyvinyl alcohol (0.4 g), followed by gelatinization and shaping into a cylinder of 3.2 cm$^2$ in cross-sectional area and 1 mm in thickness for an iontophoretic matrix for cathode.

Example 4

Human insulin (10 mg) (produced by Shimizu Pharmaceutical Co., Ltd., Japan) and tartaric acid (10 mg) were dissolved in an 8% aqueous solution of polyvinyl alcohol (1 g) (pH 3.4), followed by gelatinization and shaping into a cylinder of 8 cm$^2$ in cross-sectional area and 1 mm in thickness for an iontophoretic matrix for anode. Tartaric acid (10 mg) was dissolved in an 8% aqueous solution of polyvinyl alcohol (1 g), followed by gelatinization and shaping into a cylinder of 8 cm$^2$ in cross-sectional area and 1 mm in thickness for an iontophoretic matrix for cathode.

Example 5

Salmon calcitonin (2 mg) (SEIKAGAKU CORPORATION, Japan) and citric acid monohydrate (5 mg) were dissolved in 0.4 g of an 8% aqueous solution of polyvinyl alcohol (pH 3.4), followed by gelatinization and shaping into a cylinder of 8 cm$^2$ in cross-sectional area and 1 mm in thickness for an iontophoretic matrix for anode. Citric acid monohydrate (5 mg) was dissolved in an 8% aqueous solution of polyvinyl alcohol (0.4 g), followed by gelatinization and shaping into a cylinder of 3.2 cm$^2$ in cross-sectional area and 1 mm in thickness for an iontophoretic matrix for cathode.

Experimental Example 1 hPTH (1→34) (10 mg) was dissolved in an 8% aqueous solution of polyvinyl alcohol (1 g) (pH about 6.5), followed by gelatinization and shaping into a cylinder of 8 cm$^2$ in cross-sectional area and 1 mm in thickness for an iontophoretic matrix for anode. An 8% aqueous solution of polyvinyl alcohol (1 g) was gelatinized and shaped into a cylinder of 8 cm$^2$ in cross-sectional area and 1 mm in thickness for an iontophoretic matrix for cathode (this set of matrix for anode and cathode is referred to as comparative matrix 1).

After attaching a carbon-coated titanium electrode (hereinafter referred to as the electrode), each of the matrix of Example 1 and comparative matrix 1 was applied to the hair-removed abdominal skin of male SD rats (7 weeks of age). The rats with the matrix of Example 1 were divided into two groups: a group having periodical blood collection via the tail vain without electric supply (non-electric supply administration group), and a group with electric supply. The group with comparative matrix 1 also received electric supply. Electricity was supplied at a constant rate of 1 mA/cm$^2$ (40 kHz, on/off ratio=3/7) for 4 consecutive hours, using ADIS4030 (ADVANCE Company, Japan). The changes over time in serum HPTH (1→34) level are shown in FIG. 3. In the non-electric supply administration group, the serum hPTH (1→34) level remained as before administration even during matrix loading; in the group using comparative matrix 1, the serum hPTH (1→34) level rose to 3 times the pre-administration serum hPTH (1→34) level at 30 minutes following administration, followed by a rapid decline; the hPTH (1→34) level was same as the pre-administration serum hPTH (1→34) level during and after electric supply. In the group using the matrix of Example 1, the serum hPTH (1→34) level rose to about 5 times the pre-administration serum hPTH (1→34) level by 1 hour following administration, reaching about 30 times the pre-administration serum hPTH (1→34) level after 4 hours. This delay of rise in serum hPTH (1→34) levels is attributable to the formation of depot of hPTH ((1→34) in the skin. These results demonstrate that included carboxylic acid markedly promotes the absorption effect of iontophoreses.

Serum hPTH (1→34) levels were determined by radioimmunoassay [rat PTH kit, Immunotropics Inc. USA] (the same applies below).

Experimental Example 2 hPTH (1→34) (10 mg) and citric acid monohydrate (2.1 mg) were dissolved in an 8% aqueous solution of polyvinyl alcohol (0.4 g) (pH about 5.3), followed by gelatinization and shaping into a cylinder of 3.2 cm$^2$ in cross-sectional area and 1 mm in thickness for an iontophoretic matrix for anode. Citric acid monohydrate (7 mg) was dissolved in an 8% aqueous solution of polyvinyl alcohol (0.4 g), followed by gelatinization and shaping into a cylinder of 3.2 cm$^2$ in cross-sectional area and 1 mm in thickness for an iontophoretic matrix for cathode (this set of matrix for anode and cathode is hereinafter referred to as comparative matrix 2).

After attaching an electrode, each of the matrix of Example 3 and comparative matrix 2 was applied to the hair-removed abdominal skin of male SD rats (7 weeks of age). Electricity was supplied at a constant rate of 2 mA/cm$^2$ (40 kHz, on/off ratio=3/7) for 4 consecutive hours using ADIS4030 (produced by ADVANCE Company, Japan). The changes over time in serum hPTH (1→34) level are shown in FIG. 4. Although both groups had almost the same serum hPTH (1→34) levels during the first 4 hours of electric supply, the group using the matrix of Example 1 of lower pH showed a greater rise in serum hPTH (1→34) level after 4 hours, and the serum hPTH (1→34) level being more than 10 times greater than the serum hPTH (1→34) level of the group using the comparative matrix at 6 hours. These results demonstrate that there is an important relationship between the increase in drug absorbability and preparation pH.

Experimental Example 3 hPTH (1→34) (10 mg) and citric acid monohydrate (7 mg) were dissolved in an 8% aqueous solution of polyvinyl alcohol (1 g) (pH 3.8), followed by gelatinization and shaping into a cylinder of 8 cm$^2$ in cross-sectional area and 1 mm in thickness for an iontophoretic matrix for anode. Citric acid monohydrate (7 mg) was dissolved in an 8% aqueous solution of polyvinyl alcohol (1 g), followed by gelatinization and shaping into a cylinder of 8 cm$^2$ in cross-sectional area and 1 mm in thickness for an iontophoretic matrix for cathode. After attaching a carbon-coated titanium electrode, each matrix was applied to the hair-removed abdominal skin of rats. Electricity was supplied at a constant rate of 1.5 mA/cm$^2$ (40 kHz, on/off ratio=3/7) for 2 consecutive hours, followed by non electric supply for 2 hours, using ADIS4030 (ADVANCE Company, Japan). Electric supply was repeated under the same conditions as mentioned above. Throughout this cycle, the matrix was kept in place. Blood was collected periodically via the tail vein; serum hPTH (1→34) levels were determined. The changes over time in serum hPTH (1→34) level are shown in FIG. 5. Corresponding to the two times of electric supply, the serum hPTH (1→34) level changed, although there was a slight time lag. In addition, the maximum serum hPTH (1→34) level at each electric supply was sufficient to exhibit drug effect relating to osteogenesis as obtained by subcutaneous injection.

Experimental Example 4 hPTH (1→34) (1 mg) was dissolved in 0.8 ml of an 8% polyvinyl alcohol solution in 33 mM aqueous citric acid. This solution was poured over a silicon mold of 8 $cm^2$ surface area and 1 mm thickness and stored under freezing conditions, followed by thawing to produce an iontophoretic matrix for anode. An iontophoretic matrix for cathode of the same composition as above but containing no drug was prepared in the same manner as above. After attaching a carbon-coated titanium electrode, both matrices were applied to the abdominal skin of rats (male SD rats weighing about 250 g having their abdominal hair removed on the day before). Electricity was supplied under the following conditions; serum hPTH (1→34) levels were periodically determined to assess the absorption promoting activity of hPTH (1→34).

Electric supply conditions: pulsating direct current (40 kHz, on/off ratio=3/7, amperage 1.5 mA/$cm^2$). Electricity was supplied for 2 hours, followed by a non-electric supply period of 2 hours; this cycle was repeated twice.

The changes over time in serum hPTH (1→34) level are shown in FIG. 6. Corresponding to electric supply, high serum hPTH (1→34) levels were seen.

Experimental Example 5

The same manner as in Experimental Example 4 was followed, except that electricity was supplied under the following conditions.

Electric supply conditions: pulsating direct current (40 kHz, on/off ratio=3/7, amperage 1.5 mA/$cm^2$). Electricity was supplied for 1 hour, followed by a non-electric supply period of 1 hour; this cycle was repeated 4 times.

The changes over time in serum hPTH (1→34) level are shown in FIG. 7. Corresponding to electric supply, high serum hPTH (1→34) levels with three peaks were seen.

Experimental Example 6

The same manner as in Experimental Example 4 was followed, except that electricity was supplied under the following conditions.

Electric supply conditions: pulsating direct current (40 kHz, on/off ratio=3/7, amperage 1.5 mA/$cm^2$). Electricity was supplied for 0.5 hours, followed by a non-electric supply period of 1.5 hours; this cycle was repeated 4 times.

The changes over time in serum hPTH (1→34) level are shown in FIG. 8. Corresponding to electric supply, high serum hPTH (1→34) levels with two peaks were seen.

Experimental Example 7

The same manner as in Experimental Example 4 was followed, except that electricity was supplied under the following conditions.

Electric supply conditions: pulsating direct current (40 kHz, on/off ratio=3/7, amperage 1.5 mA/$cm^2$). Electricity was supplied for 0.5 hours, followed by a non-electric supply period of 0.5 hours; this cycle was repeated 2 times; subsequently electricity was supplied for 0.5 hours, followed by a nonelectric supply period of 1.5 hours; this cycle was repeated 4 times, The changes over time in serum hPTH (1→34) level are shown in FIG. 9. Corresponding to electric supply, high serum hPTH (1→34) levels with four peaks were seen.

Experimental Example 8

The same manner as in Experimental Example 4 was followed, except that electricity was supplied under the following conditions.

Electric supply conditions: pulsating direct current (40 kHz, on/off ratio=3/7, amperage 2 mA/$cm^2$). Electricity was supplied for 0.25 hours, followed by a non-supply period of 1.75 hours; this cycle was repeated 4 times.

The changes over time in serum hPTH (1→34) level are shown in FIG. 10. Corresponding to electric supply, high serum hPTH (1→34) levels with two peaks were seen.

By the following Examples and Experimental Examples, the present invention, which is concerned with a matrix for iontophoreses, which comprises a drug reservoir containing a drug, the reservoir having a thickness of less than 0.05 mm, is will be described in further detail, but they do not intend to limit the invention in any manner. Percent figures in Examples and Experimental Examples are % by weight/volume, unless otherwise stated.

Example 6

To 1 ml of a 50 mM aqueous solution of citric acid containing 1% of hPTH (1→34) as produced in Reference Example 1, 4 ml of a 6.25% ethyl alcohol solution of hydroxypropyl cellulose (hereinafter abbreviated as HPCL), (Nippon Soda Co., Ltd., Japan) was added, to yield a uniform solution.

This solution (0.5 g) was poured in a cylindrical silicon rubber pit of 8 $cm^2$ in base area and about 1 mm in thickness, followed by alcohol evaporation at normal temperature (25° C.) under normal pressure (1 atm). A cylindrical drug reservoir of 8 $cm^2$ in cross-sectional area, 27 mg in weight and 0.024 mm in thickness containing 1 mg of hPTH (1→34), was produced.

Example 7

A solution (1 g) comprising hPTH (1→34) and HPC-L, as produced in the same manner as in Example 6, was poured in a cylindrical silicon rubber pit of 16 $cm^2$ in base area and about 1 mm in thickness, followed by alcohol evaporation at normal temperature (25° C.) under normal pressure (1 atm). A cylindrical drug reservoir of 16 $cm^2$ in cross-sectional area, 54 mg in weight and 0.024 mm in thickness containing 2 mg of hPTH (1→34), was produced.

Example 8

A solution (0.2 g) comprising hPTH (1→34) and HPC-L, as produced in the same manner as in Example 6, was poured in a cylindrical silicon rubber pit of 3.2 $cm^2$ in base area and about 1 mm in thickness, followed by alcohol evaporation at normal temperature (25° C.) under normal pressure (1 atm). A cylindrical drug reservoir of 3.2 $cm^2$ in cross-sectional area, 10 mg in weight and 0.022 mm in thickness containing 0.4 mg of hPTH (1→34), was produced.

Example 9

The same procedure as in Example 6 was followed, except that a 3.125% ethyl alcohol solution of HPC-L was used in place of the 6.25% ethyl alcohol solution of HPC-L, to yield a cylindrical matrix for iontophoreses of 8 cm$^2$ in cross-sectional area, 14.5 mg in weight and 0.013 mm in thickness containing 1 mg of hPTH (1→34).

Example 10

The same procedure as in Example 6 was followed, except that a 12.5% ethyl alcohol solution of HPC-L was used in place of the 6.25% ethyl alcohol solution of HPC-L. A cylindrical drug reservoir of 8 cm$^2$ in cross-sectional area, 52 mg in weight and 0.046 mm in thickness containing 1 mg of hPTH (1→34), was produced.

Example 11

The same procedure as in Example 6 was followed, except that a 50 mM aqueous solution of citric acid containing 0.2% HPTH (1→34) was used in place of the 50 mM aqueous solution of citric acid containing 1% hPTH (1→34). A cylindrical drug reservoir of 8 cm$^2$ in cross-sectional area, 26.2 mg in weight and 0.023 mm in thickness containing 0.2 mg of hPTH (1→34), was produced.

Example 12

The same procedure as in Example 6 was followed, except that a 50 mM aqueous solution of citric acid containing 2% hPTH (1→34) was used in place of the 50 mM aqueous solution of citric acid containing 1% hPTH (1→34). A cylindrical drug reservoir of 8 cm$^2$ in cross-sectional area, 28 mg in weight and 0.025 mm in thickness containing 2 mg of hPTH (1→34), was produced.

Example 13

The same procedure as in Example 6 was followed, except that a 50 mM aqueous solution of citric acid containing 4% hPTH (1→34) was used in place of the 50 mM aqueous solution of citric acid containing 1% hPTH (1→34). A cylindrical drug reservoir of 8 cm$^2$ in cross-sectional area, 30 mg in weight and 0.027 mm in thickness containing 4 mg of hPTH (1→34), was produced.

Example 14

The same procedure as in Example 6 was followed, except that a 6.25% ethyl alcohol dispersion of hydroxypropylmethyl cellulose (TC-5) (Shin-Etsu Chemical Co., Ltd., Japan) was used in place of the 6.25% ethyl alcohol solution of HPC-L. A cylindrical drug reservoir of 8 cm$^2$ in cross-sectional area, 27 mg in weight and 0.024 mm in thickness containing 1 mg of hPTH (1→34), was produced. TC-5 occurs as a colloidal dispersion in 100% ethyl alcohol; after being mixed with a 50 mM citric acid solution containing 1% hPTH (1→34), TC-5 colloids dissolved.

Example 15

The same procedure as in Example 6 was followed, except that an ethyl alcohol solution containing 3.125% HPC-L and 3.125% methyl cellulose (Metlose SM) (Shin-Etsu Chemical Co., Ltd., Japan) was used in place of the 6.25% ethyl alcohol solution of HPC-L. A cylindrical drug reservoir of 8 cm$^2$ in cross-sectional area, 27 mg in weight and 0.024 mm in thickness containing 1 mg of hPTH (1→34), was produced.

Example 16

The same procedure as in Example 6 was followed, except that a 50 mM aqueous solution of citric acid containing 0.2% salmon calcitonin (hereinafter abbreviated as sCT) (Sigma Company, USA) was used in place of the 50 mM aqueous solution of citric acid containing 1% hPTH (1→34). A cylindrical drug reservoir of 8 cm$^2$ in cross-sectional area, 26.2 mg in weight and 0.023 mm in thickness containing 0.2 mg of sCT, was produced.

Example 17

The same procedure as in Example 6 was followed, except that a 50 mM aqueous solution of citric acid containing 0.02% sCT was used in place of the 50 mM aqueous solution of citric acid containing 1% hPTH (1→34). A cylindrical drug reservoir of 8 cm$^2$ in cross-sectional area, 26 mg in weight and 0.023 mm in thickness containing 0.02 mg of sCT, was produced.

Example 18

The same procedure as in Example 6 was followed, except that a 50 mM aqueous solution of citric acid containing 1% bovine pancreatic insulin (Wako Pure Chemical Industries, Japan) was used in place of the 50 mM aqueous solution of citric acid containing 1% hPTH (1→34). A cylindrical drug reservoir of 8 cm$^2$ in cross-sectional area, 27 mg in weight and 0.023 mm in thickness containing 1 mg of bovine pancreatic insulin, was produced.

Example 19

The same procedure as in Example 6 was followed, except that a 50 mM aqueous solution of citric acid containing 1% TRH [produced by the method described in the International Journal of Pharmaceutics, Vol. 69, pp. 69–75 (1991)] was used in place of the 50 mM aqueous solution of citric acid containing 1% hPTH (1→34). A cylindrical drug reservoir of 8 cm$^2$ in cross-sectional area, 27 mg in weight and 0.023 mm in thickness containing 1 mg of TRH, was produced.

Example 20

The same procedure as in Example 6 was followed, except that a 50 mM aqueous solution of citric acid containing 0.2% leuprolide (Takeda Chemical Industries, Japan) was used in place of the 50 mM aqueous solution of citric acid containing 1% hPTH (1→34). A cylindrical drug reservoir of 8 cm$^2$ in cross-sectional area, 26.2 mg in weight and 0.023 mm in thickness containing 0.2 mg of leuprolide, was produced.

Experimental Example 9

To the surface of a cylinder electrode matrix of 8 cm$^2$ in cross-sectional area and 1 mm in thickness as produced by gelatinization and shaping an 8% aqueous solution of polyvinyl alcohol, each of the drug reservoirs produced in Examples 6 through 20 was attached. Each drug reservoir dissolved within 1 minute after attachment.

A matrix containing no hPTH (1→34) was produced in the same manner as in Example 6, and brought into contact with damped skin in the upper arm. The matrix dissolved within 1 minute after application.

Experimental Example 10

To the surface of a cylinder electrode matrix of 8 cm$^2$ in cross-sectional area and 1 mm in thickness as produced by gelatinization and shaping a 33 mM aqueous solution (0.8 ml) of citric acid containing 8% polyvinyl alcohol, the drug reservoir of Example 6 was attached after being peeled off from the silicon mold using pincettes, to produce a matrix for anode. Separately, a cylinder matrix of 8 cm² in cross-sectional area and 1 mm in thickness as produced by gelatinization and shaping a 33 mM aqueous solution (0.8 ml) of citric acid containing 8% polyvinyl alcohol was used as a matrix for cathode. After attaching a carbon-coated titanium electrode, each matrix was applied to the hair-removed abdominal skin of a male SD rat (about 250 g body weight). For the matrix for anode, in particular, the face to which the drug reservoir of Example 6 was applied was brought into contact with the abdomen.

In applying the matrixes for anode and cathode to the rat, the rat was anesthetized with ether, after which the matrix for anode, to which the drug reservoir of Example 6 was applied, and the matrix for cathode, were brought into contact with the rat abdomen and fixed with elastic bandage. The rat was then immobilized in a Borman cage.

Pulsating direct current (40 kHz; ON/OFF ratio=3/7; amperage 1.5 mA/cm²) was supplied for 1 hour, using ADIS4030 (produced by ADVANCE Company, Japan).

Serum hPTH (1→34) levels were determined by radio-immunoassay [Rat PTH Kit, Immutopics, Inc., USA].

After 1 hour of electric supply, the serum hPTH (1→34) level reached a maximum (about 840 pg/ml). This result demonstrates that rapid absorption and high bioavailability are achieved by using the matrix for iontophoresis of, which comprises the drug reservoir of Example 6 and a electrode matrix.

Experimental Example 11

The same procedure as in Experimental Example 10 was followed, except that the drug reservoir of Example 16 was used in place of the drug reservoir of Example 6, to evaluate the percutaneous absorbability of sCT, by monitoring the time-related changes in serum calcium level.

Serum calcium levels were determined using a blood calcium assay kit (Calcium E-Test Wako, Wako Pure Chemical Industries, Japan).

The changes over time in serum calcium level are shown in FIG. 11. The calcium levels at 1 and 2 hours after sCT administration were significantly lower than the normal level before sCT administration, demonstrating rapid absorption of sCT.

Experimental Example 12

The same procedure as in Experimental Example 10 was followed, except that iontophoresis was performed under the following electric supply conditions, to evaluate the promotion of percutaneous absorption of HPTH (1→34).
Electric Supply Conditions:

Using a pulsating direct current (40 kHz, ON/OFF ratio=3/7, amperage 1.5 A/cm²), electricity was supplied for 1 hour, followed by a nonelectric supply period of 1 hour; this cycle was repeated 4 times.

The changes over time in serum hPTH (1→34) level are shown in FIG. 12. Corresponding to electric supply, high serum hPTH (1→34) levels were seen with three peaks.

Experimental Example 13

The same procedure as in Experimental Example 11 was followed, except that iontophoresis was performed under the following electric supply conditions, to evaluate the promotion of percutaneous absorption of sCT. Electric supply conditions:

Using a pulsating direct current (40 kHz, ON/OFF ratio=3/7, amperage 1.5 A/cm²), electricity was supplied for 1 hour, followed by a nonelectric supply period of 1 hour; this cycle was repeated 4 times.

The changes over time in serum calcium level are shown in FIG. 13. It is evident that significantly decreased serum calcium levels (about 60–65% of pre-administration normal values) are retained for a long period.

Experimental Example 14

To a sheet of released paper (Takara Co., Ltd, Japan), previously coated with a thin layer of glue (Kokuyo Co., Ltd., Japan), the drug reservoir of Example 6 was applied by gentle pressing. A cylinder electrode matrix of 8 cm² in cross-sectional area and 1 mm in thickness as produced by gelling and shaping an 8% aqueous solution of polyvinyl alcohol was brought into contact with the thus-treated drug reservoir; after appropriate pressing, the released paper was removed, to leave the drug reservoir on a cross-section of the cylindrical gel.

Experimental Example 15

After the sCT-containing drug reservoir of Example 16 was stored at room temperature (25° C.) for 1 week, the sCT content reduction in the drug reservoir was determined by high performance liquid chromatography (HPLC).

HPLC conditions: column, GL-PACK (GL Science Ltd.); elution method, gradient method [solvent A 0.1% (v/v) aqueous solution of trifluoroacetic acid, solvent B acetonitrile containing 0.1% (v/v) trifluoroacetic acid; linear gradient from 80/20 (v/v) to 50/50 (v/v) solvent A/solvent B ratio; detection wavelength 280 nm UV.

As a result, the percent reduction in sCT content was 0%; sCT proved stable in the drug reservoir of Example 16.

Figure 1:
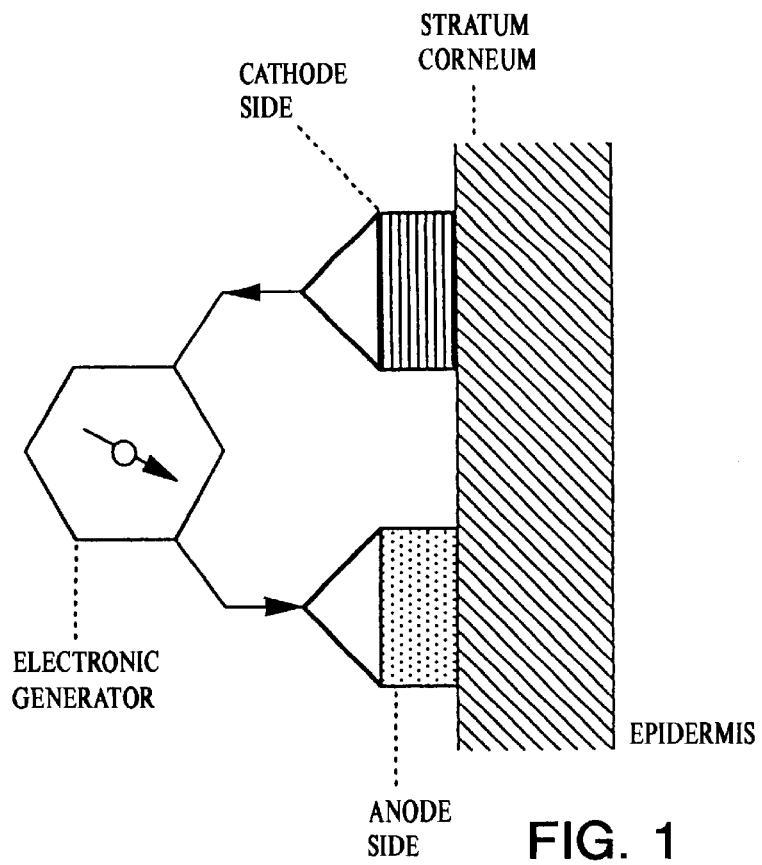
FIG. 1 is a diagram portraying a system for iontophoreses, which comprises an anode side matrix and a cathode side matrix, wherein the anode side matrix contains a cationized drug and the cathode side matrix contains a water-soluble acidic substance.
Figure 2:
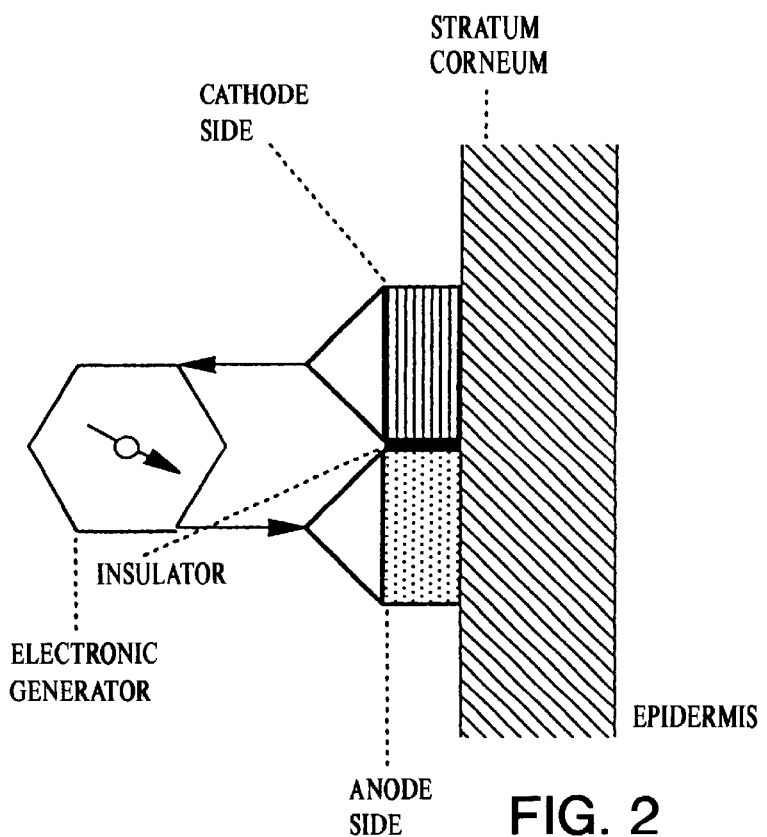
FIG. 2 is a diagram portraying a system for iontophoreses, wahich comprises an anode side matrix and a cathode side matrix, wherein the anode side matrix contains a cationized drug and the cathode side matrix contains a water-soluble acidic substance.
Figure 3:
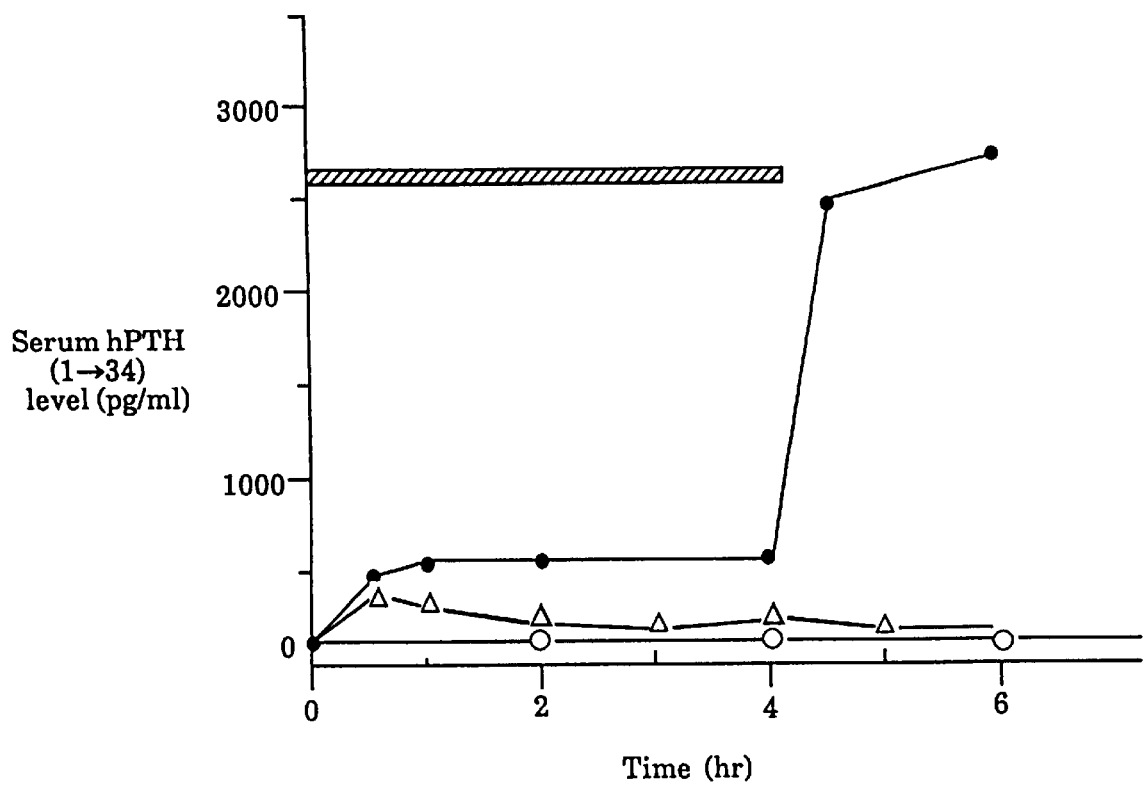
FIG. 3 shows the changes over time in serum hPTH (1→34) level in Experimental Example 1.

—○— in FIG. 3 indicates the non-electric supply administration group.

—Δ— in FIG. 3 indicates comparative matrix 1.

—●— in FIG. 3 indicates the matrix of Example 1.

▨ in FIG. 3 indicates the duration of electric supply.

Figure 4:
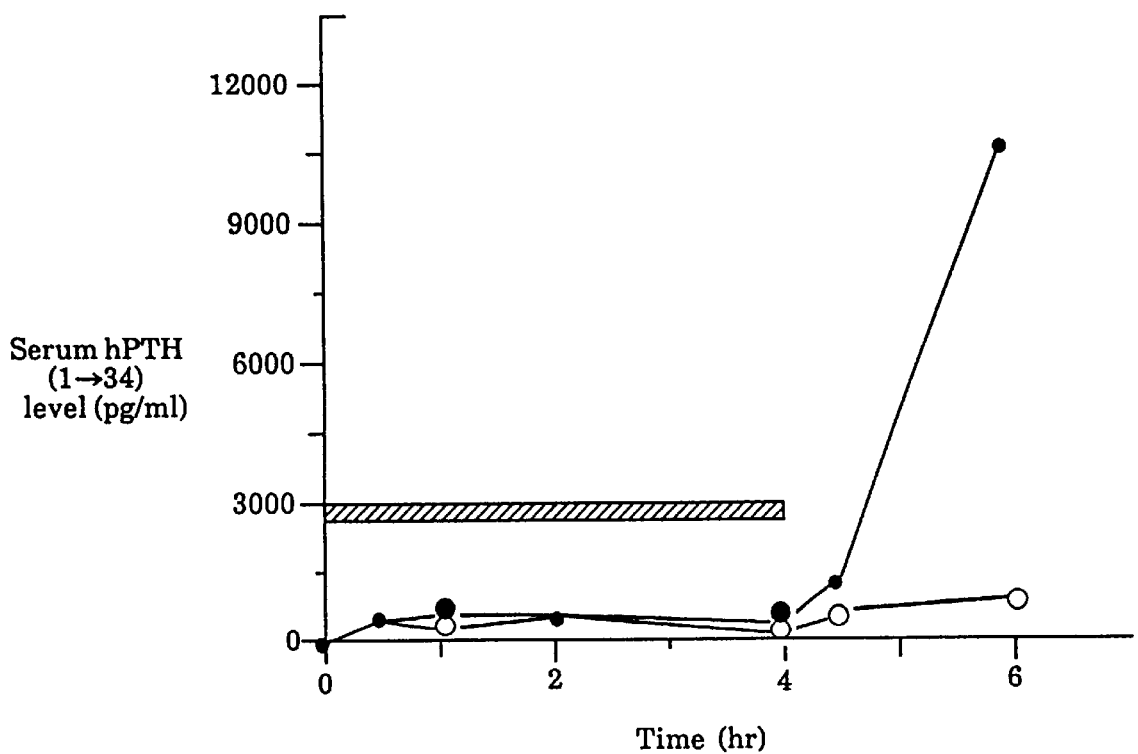
FIG. 4 shows the changes over time in serum HPTH (1→34) level in Experimental Example 2.

—○— in FIG. 4 indicates comparative matrix 2.

—●— in FIG. 4 indicates the matrix of Example 3.

▨ in FIG. 4 indicates the duration of electric supply.

Figure 5:
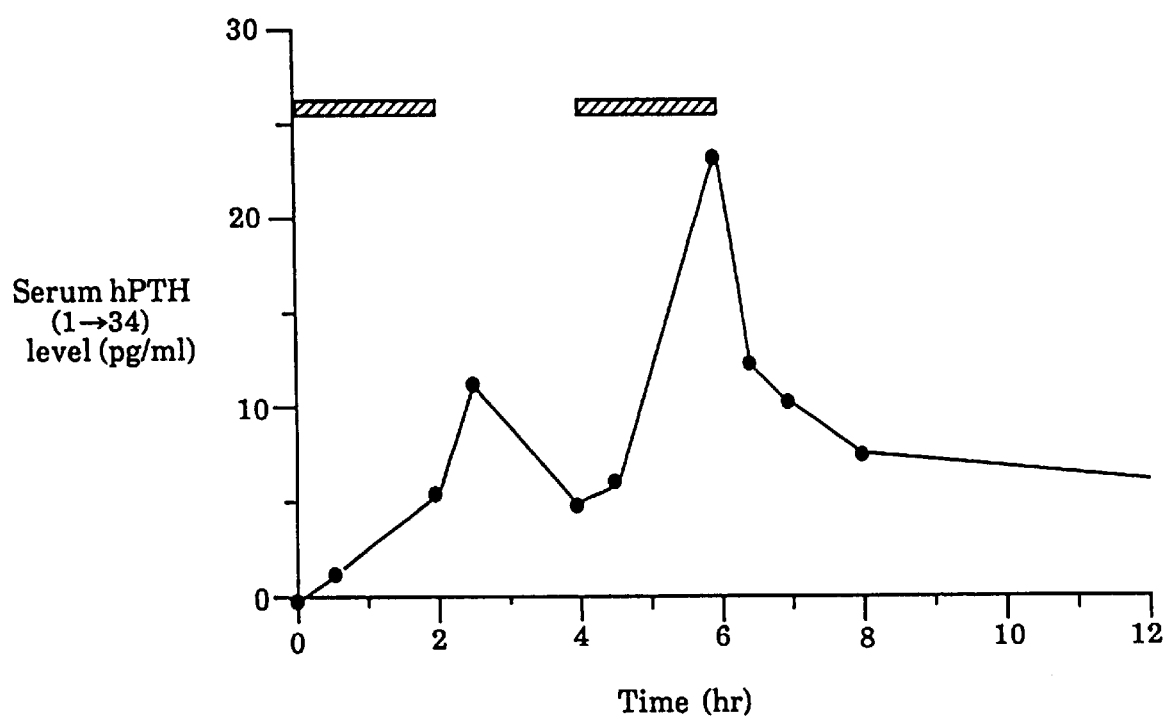
FIG. 5 shows the changes over time in serum hPTH (1→34) levels in Experimental Example 3.

▨ in FIG. 5 indicates the duration of electric supply.

Figure 6:
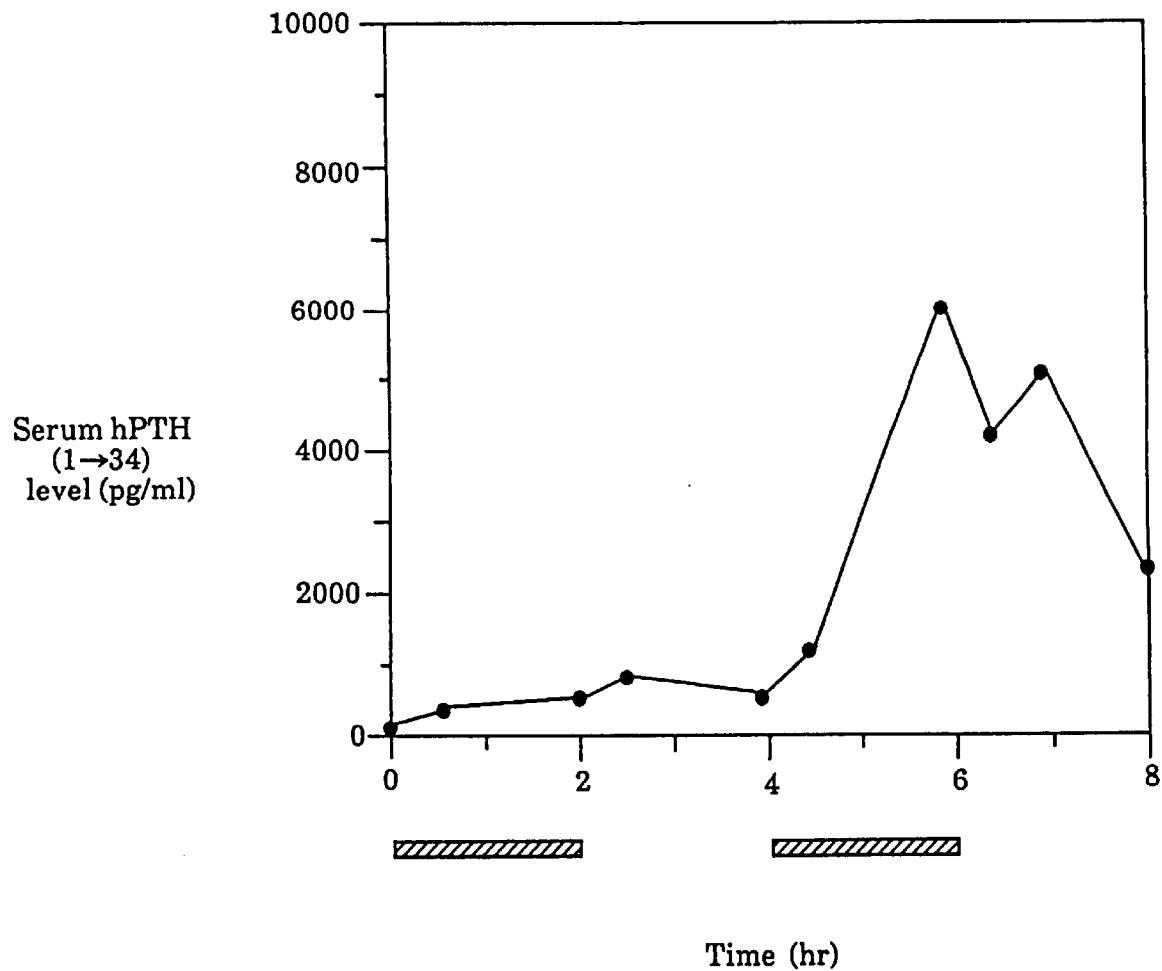
FIG. 6 shows the changes over time in serum hPTH (1→34) level in Experimental Example 4.

▨ in FIG. 6 indicates the duration of electric supply.

Figure 7:
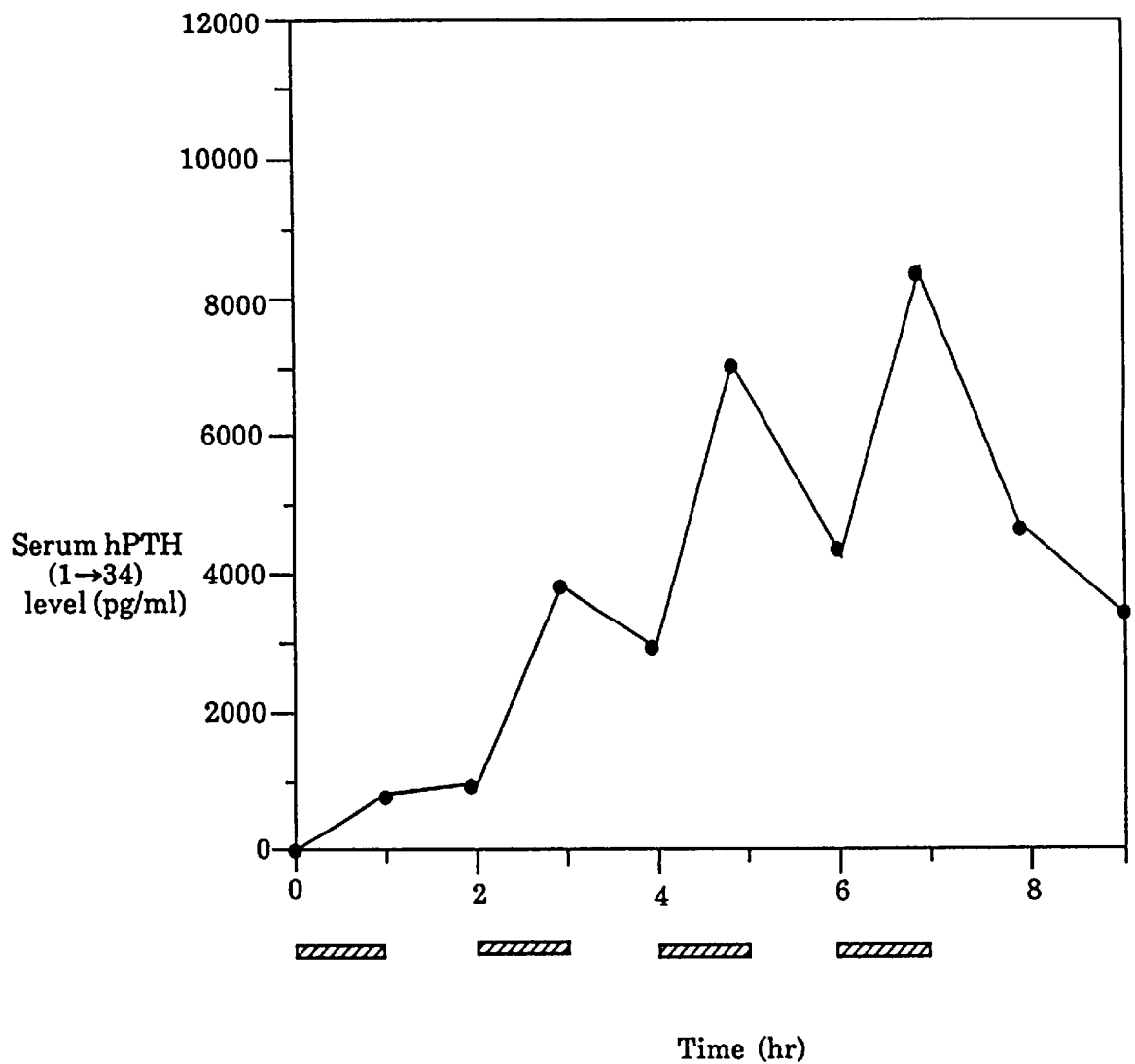
FIG. 7 shows the changes over time in serum hPTH (1→34) level in Experimental Example 5.

▨ in FIG. 7 indicates the duration of electric supply.

Figure 8:
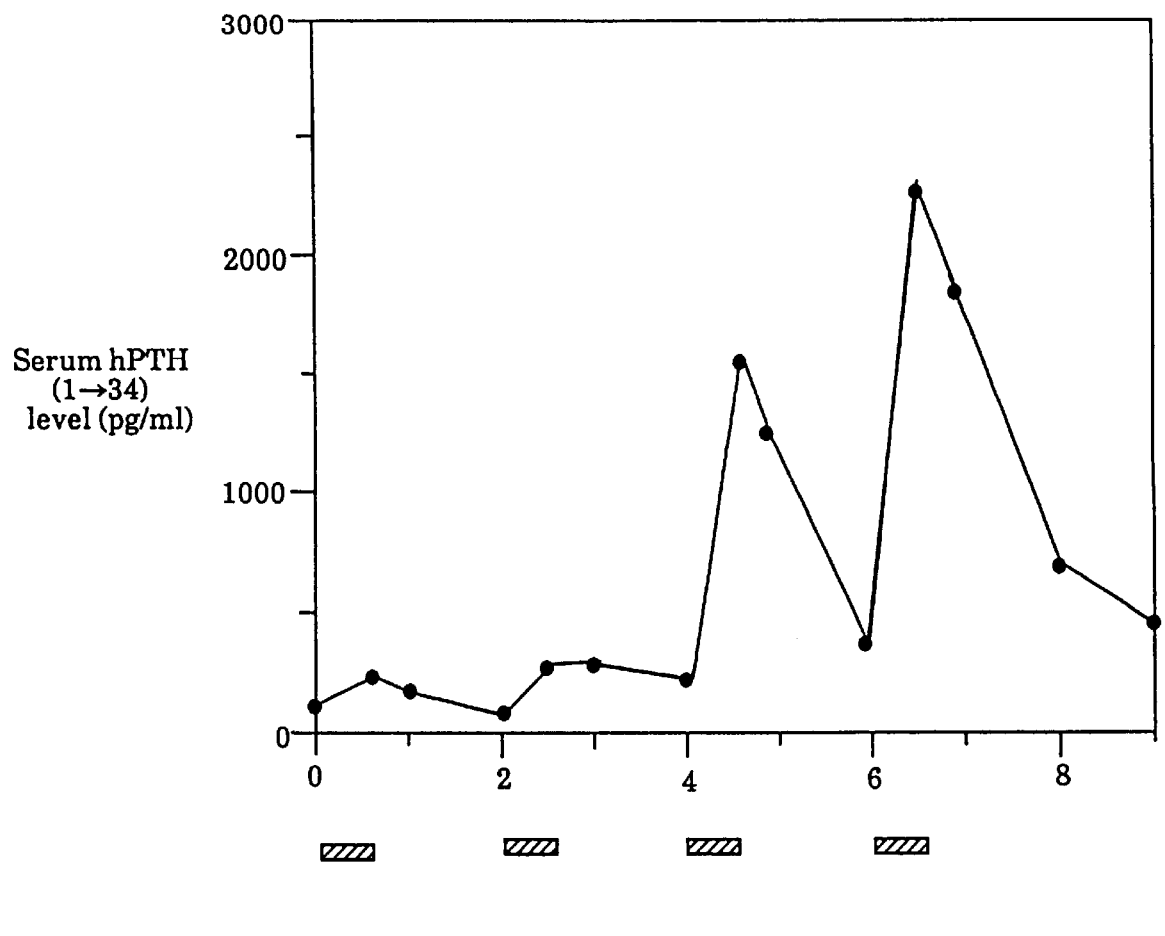
FIG. 8 shows the changes over time in serum hPTH (1→34) level in Experimental Example 6.

▨ in FIG. 8 indicates the duration of electric supply.

Figure 9:
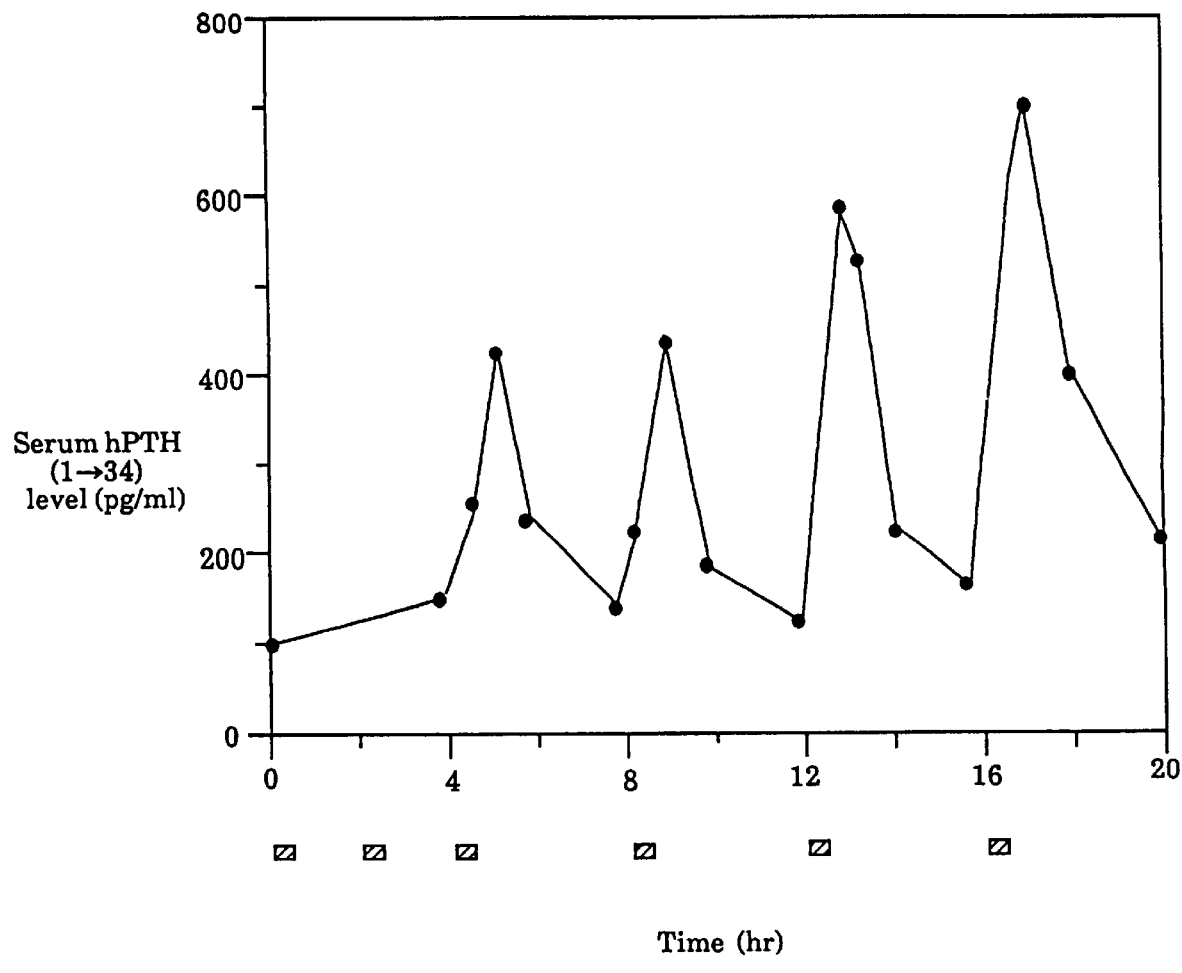
FIG. 9 shows the changes over time in serum hPTH (1→34) level in Experimental Example 7.

▨ in FIG. 9 indicates the duration of electric supply.

Figure 10:
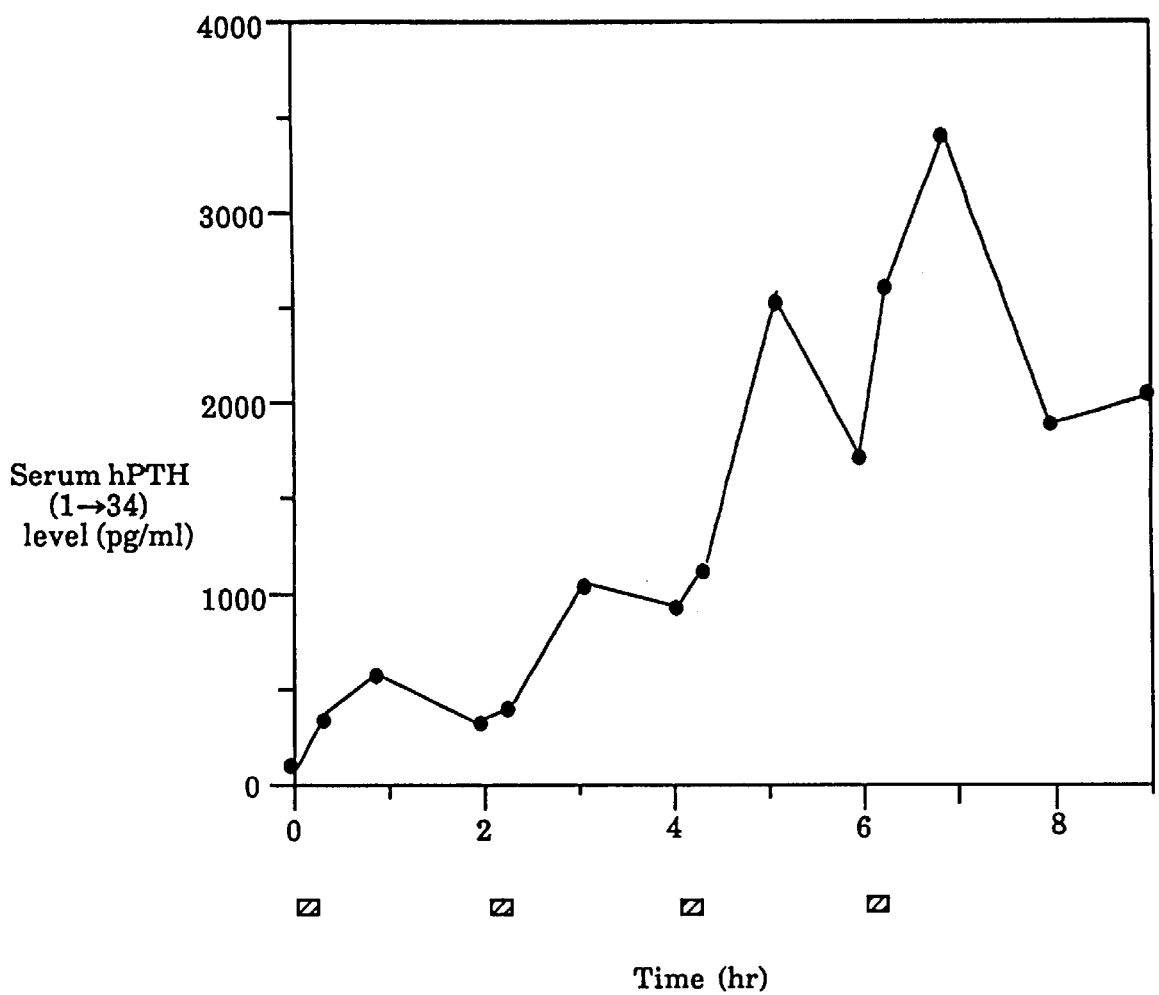
FIG. 10 shows the changes over time in serum hPTH (1→34) level in Experimental Example 8.
Figure 11:
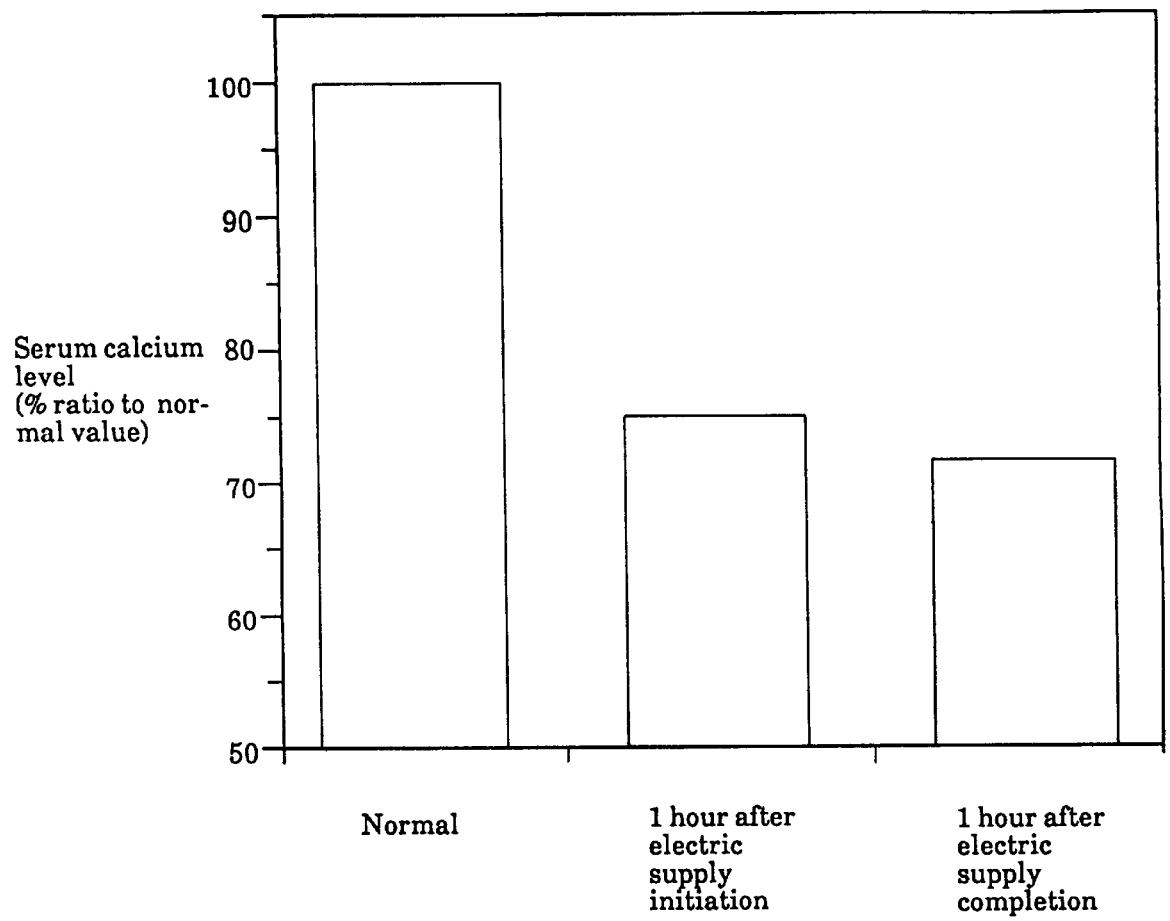
FIG. 11 shows the changes over time in serum calcium level in Experimental Example 11.

▨ in FIG. 10 indicates the duration of electric supply.

Figure 12:
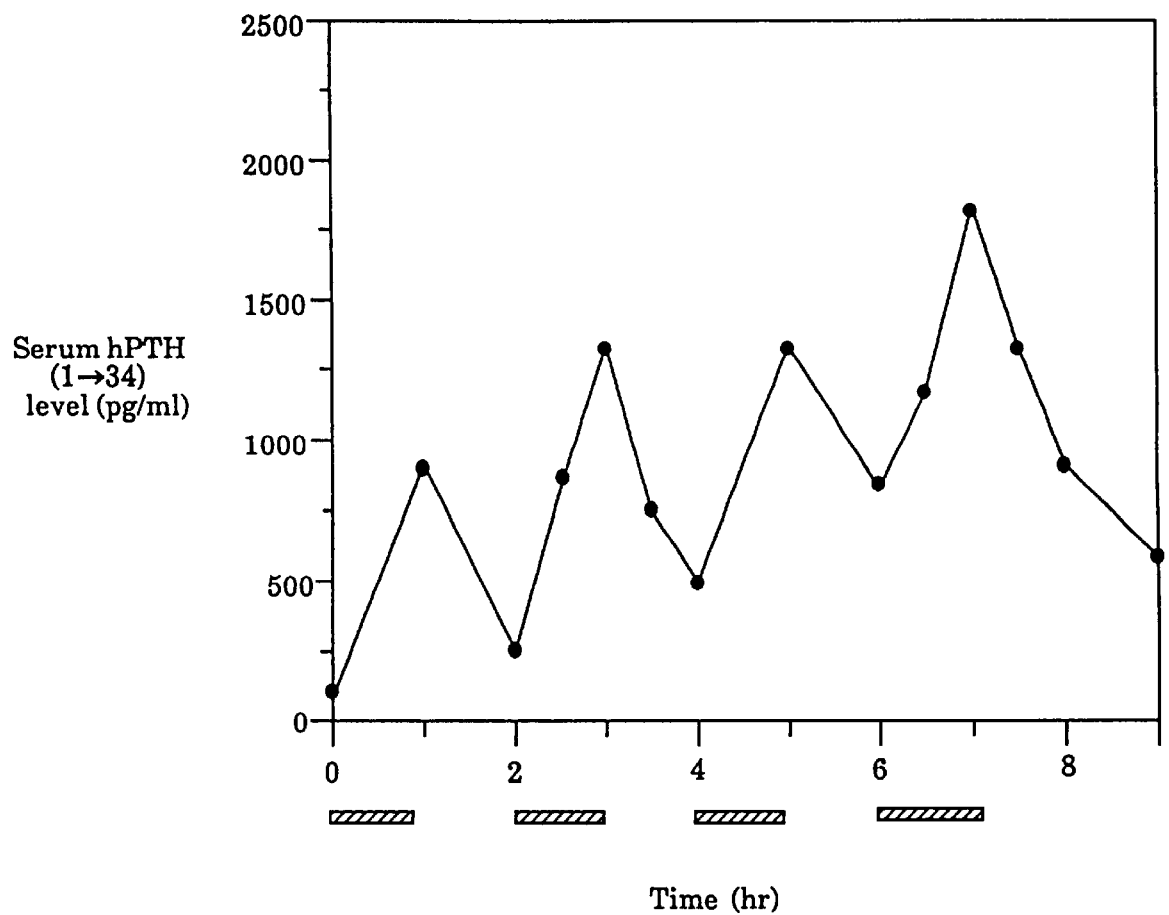
FIG. 12 shows the changes over time in serum hPTH (1→34) level in Experimental Example 12.

▨ in FIG. 12 indicates the duration of electric supply.

Figure 13:
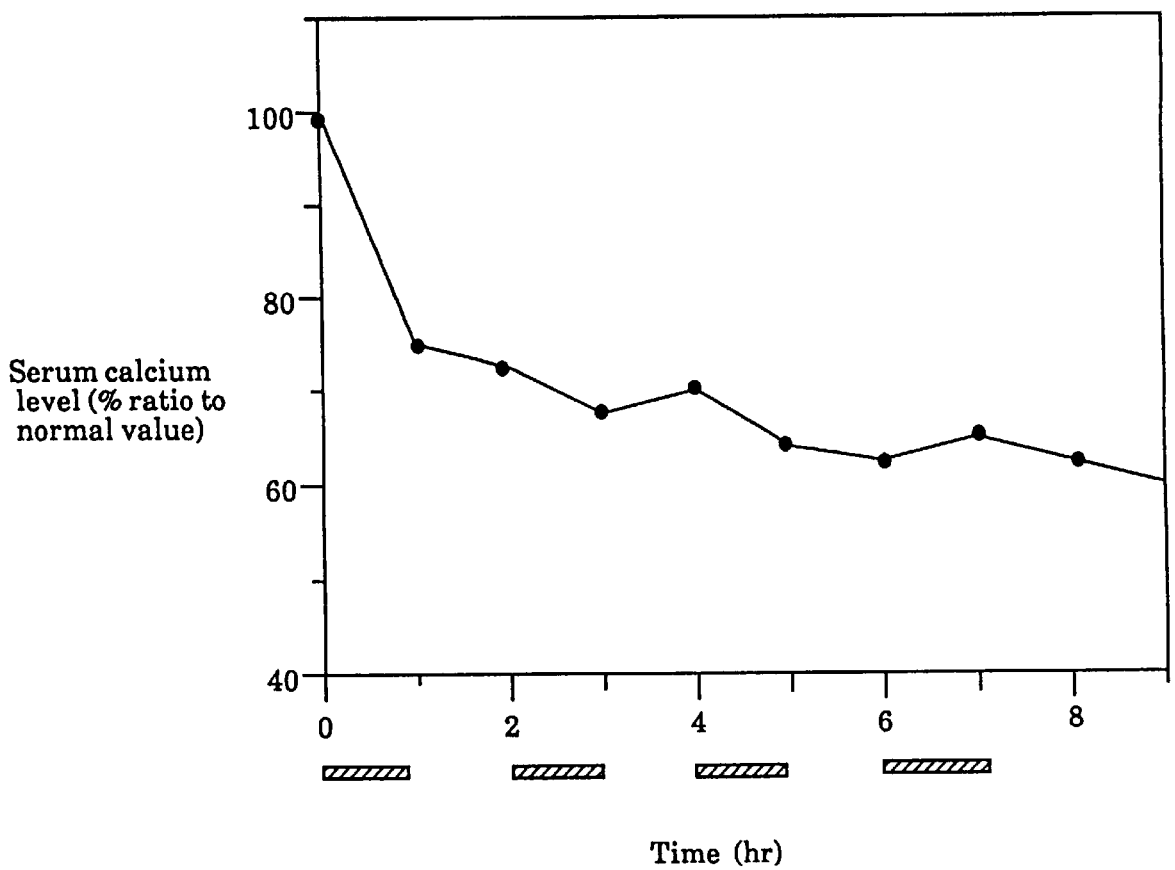
FIG. 13 shows the changes over time in serum calcium level in Experimental Example 13.

▨ in FIG. 13 indicates the duration of electric supply.

What is claimed is:

1. A method for iontophoreses, which comprises providing a system for iontophoreses comprising an anode, a cathode, a power source for supplying a pulsating direct current, an anode side matrix and a cathode side matrix, wherein the anode side matrix contains a drug cationized with a water-soluble carboxylic acid and the cathode side matrix contains a water-soluble acidic substance but does not contain any drug, and supplying an electric charge intermittently to the system to administer the drug, and wherein the pulsating direct current is applied repeatedly with a continuous electric supply period of about 15 minutes to 2 hours, followed by a non-electric supply period of about 10 minutes to 4 hours, and the total electric supply period of not more than 24 hours.

2. The method according to claim 1, wherein the electric charge is supplied repeatedly at least three times.

3. The method according to claim 1, wherein the electric charge is supplied with the pulsating direct current at a current density in the range of 0.01 to 4 mA/cm$^2$.

4. A system for iontophoreses, which comprises an anode side matrix, a cathode side matrix and a means for supplying electric charge intermittently to said anode or cathode side matrix, wherein the anode side matrix contains a drug cationized with a water-soluble carboxylic acid and the cathode side matrix contains a water-soluble acidic substance but does not contain any drug, and wherein the means for supplying electric charge supplies a pulsating direct current repeatedly with a continuous electric supply period of about 15 minutes to 2 hours, followed by a non-electric supply period of about 10 minutes to 4 hours, and the total electric supply period of not more than 24 hours.

5. The system according to claim 4, wherein the electric charge is supplied repeatedly at least three times.

6. The system according to wherein the means for supplying electric charge supplies the pulsating direct current at a current density in the range of 0.01 to 4 mA/cm$^2$.

* * * * *

UNITED STATES PATENT AND TRADEMARK OFFICE
CERTIFICATE OF CORRECTION

PATENT NO. : 6,416,503 B1
DATED : July 9, 2002
INVENTOR(S) : Yasuyuki Suzuki et al.

It is certified that error appears in the above-identified patent and that said Letters Patent is hereby corrected as shown below:

Column 24,
Line 27, after "according to" insert -- claim 4, --.

Signed and Sealed this

Seventeenth Day of December, 2002

JAMES E. ROGAN
*Director of the United States Patent and Trademark Office*